(12) United States Patent
Barrall et al.

(10) Patent No.: US 12,372,511 B2
(45) Date of Patent: *Jul. 29, 2025

(54) OSMOTIC IMBALANCE METHODS FOR BILAYER FORMATION

(71) Applicant: Roche Sequencing Solutions, Inc., Pleasanton, CA (US)

(72) Inventors: Geoffrey Barrall, San Jose, CA (US); Licheng Niu, San Jose, CA (US); Pirooz Parvarandeh, Los Altos Hills, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/658,103

(22) Filed: May 8, 2024

(65) Prior Publication Data
US 2024/0377381 A1 Nov. 14, 2024

Related U.S. Application Data

(63) Continuation of application No. 16/219,464, filed on Dec. 13, 2018, now Pat. No. 12,000,822, which is a
(Continued)

(51) Int. Cl.
*G01N 33/487* (2006.01)
*B01D 69/12* (2006.01)
(Continued)

(52) U.S. Cl.
CPC ....... *G01N 33/48721* (2013.01); *B01D 69/12* (2013.01); *G01N 15/131* (2024.01);
(Continued)

(58) Field of Classification Search
CPC ........... G01N 33/48721; G01N 15/131; G01N 15/134; B01D 69/12
See application file for complete search history.

(56) References Cited

U.S. PATENT DOCUMENTS 8,986,932 B2 3/2015 Turner
9,557,294 B2 1/2017 Chen et al.
(Continued)

FOREIGN PATENT DOCUMENTS

CN 1662662 B 10/2012
CN 103827320 A 4/2017
(Continued)

OTHER PUBLICATIONS

International search report and written opinion mailed on Sep. 4, 2017 in corresponding PCT application No. PCT/EP2017/065626 filed on Jun. 26, 2017.
(Continued)

*Primary Examiner* — Mathieu D Vargot
(74) *Attorney, Agent, or Firm* — FisherBroyles, LLP; Jason M. Pass

(57) ABSTRACT

A method of forming a plurality of lipid bilayers over an array of cells in a nanopore based sequencing chip is disclosed. Each of the cells comprises a well. A first salt buffer solution with a first osmolarity is flowed over a cell in the nanopore based sequencing chip to substantially fill a well in the cell with the first salt buffer solution. A lipid and solvent mixture is flowed over the cell to deposit a lipid membrane over the well that encloses the first salt buffer solution in the well. A second salt buffer solution with a second osmolarity is flowed above the well to reduce the thickness of the lipid membrane, wherein the second osmolarity is a lower osmolarity than the first osmolarity such that an osmotic imbalance is created between a first volume inside the well and a second volume outside the well.

13 Claims, 20 Drawing Sheets

Related U.S. Application Data continuation of application No. PCT/EP2017/065626, filed on Jun. 26, 2017.

(60) Provisional application No. 62/355,140, filed on Jun. 27, 2016.

(51) Int. Cl.
*G01N 15/12* (2006.01)
*B82Y 40/00* (2011.01)
*C12Q 1/6869* (2018.01)

(52) U.S. Cl.
CPC ............ *G01N 15/134* (2024.01); *B82Y 40/00* (2013.01); *C12Q 1/6869* (2013.01); *Y10S 977/713* (2013.01); *Y10S 977/84* (2013.01)

(56) References Cited

U.S. PATENT DOCUMENTS

| | | | |
|---|---|---|---|
| 9,850,534 | B2 | 12/2017 | Davis et al. |
| 10,155,979 | B2 * | 12/2018 | Wahba ................. C12Q 1/6869 |
| 10,246,741 | B2 | 4/2019 | Clarke |
| 10,465,240 | B2 * | 11/2019 | Wahba ............. G01N 33/48721 |
| 10,577,653 | B2 * | 3/2020 | Barrall ............. G01N 27/44791 |
| 12,000,822 | B2 * | 6/2024 | Barrall ................. G01N 15/131 |
| 2007/0161101 | A1 | 7/2007 | Takeuchi |
| 2013/0123450 | A1 | 5/2013 | Takarada |
| 2013/0188841 | A1 | 7/2013 | Pollock |
| 2014/0034497 | A1 | 2/2014 | Davis et al. |
| 2014/0364324 | A1 | 12/2014 | Turner |
| 2015/0152492 | A1 | 6/2015 | Brown et al. |
| 2015/0153302 | A1 * | 6/2015 | Davis ............... G01N 33/48721 <br> 204/403.08 |
| 2016/0178554 | A1 | 6/2016 | Chen et al. |
| 2017/0283866 | A1 | 10/2017 | Wahba et al. |
| 2017/0283867 | A1 | 10/2017 | Wahba et al. |

FOREIGN PATENT DOCUMENTS

| | | |
|---|---|---|
| CN | 104651500 B | 6/2017 |
| CN | 105637081 B | 6/2018 |
| CN | 104254619 A | 8/2018 |
| JP | 2016015803 A | 1/2016 |
| JP | 2017131182 A | 8/2017 |
| WO | 2012/095660 A2 | 7/2012 |
| WO | 2015061510 A1 | 4/2015 |

OTHER PUBLICATIONS

International Search Report dated Aug. 22, 2017 and the Written Opinion issued in corresponding PCT application No. PCT/EP2017/065782 filed on Jun. 27, 2017 (eleven pages).

Li-Qun Gu et al, Electroosmotic enhancement of the binding of a neutral molecule to a transmembrane pore, PNAS, vol. 100, No. 26, pp. 15498-15503, (2003).

Noskov et al, 2004, "Ion Permeation through the [alpha]-Hemolysin Channel: Theoretical Studies Based on Brownian Dynamics and Poisson-Nernst-Plank Electrodiffusion Theory", Biophysical Journal, 87(4):2299-2309.

Schibel et al, 2011, "Fluorescence Microscopy of the Pressure-Dependent Structure of Lipid Bilayers Suspended across Conical Nanopores", Journal of the American Chemical Society, 133(20):7810-7815.

* cited by examiner

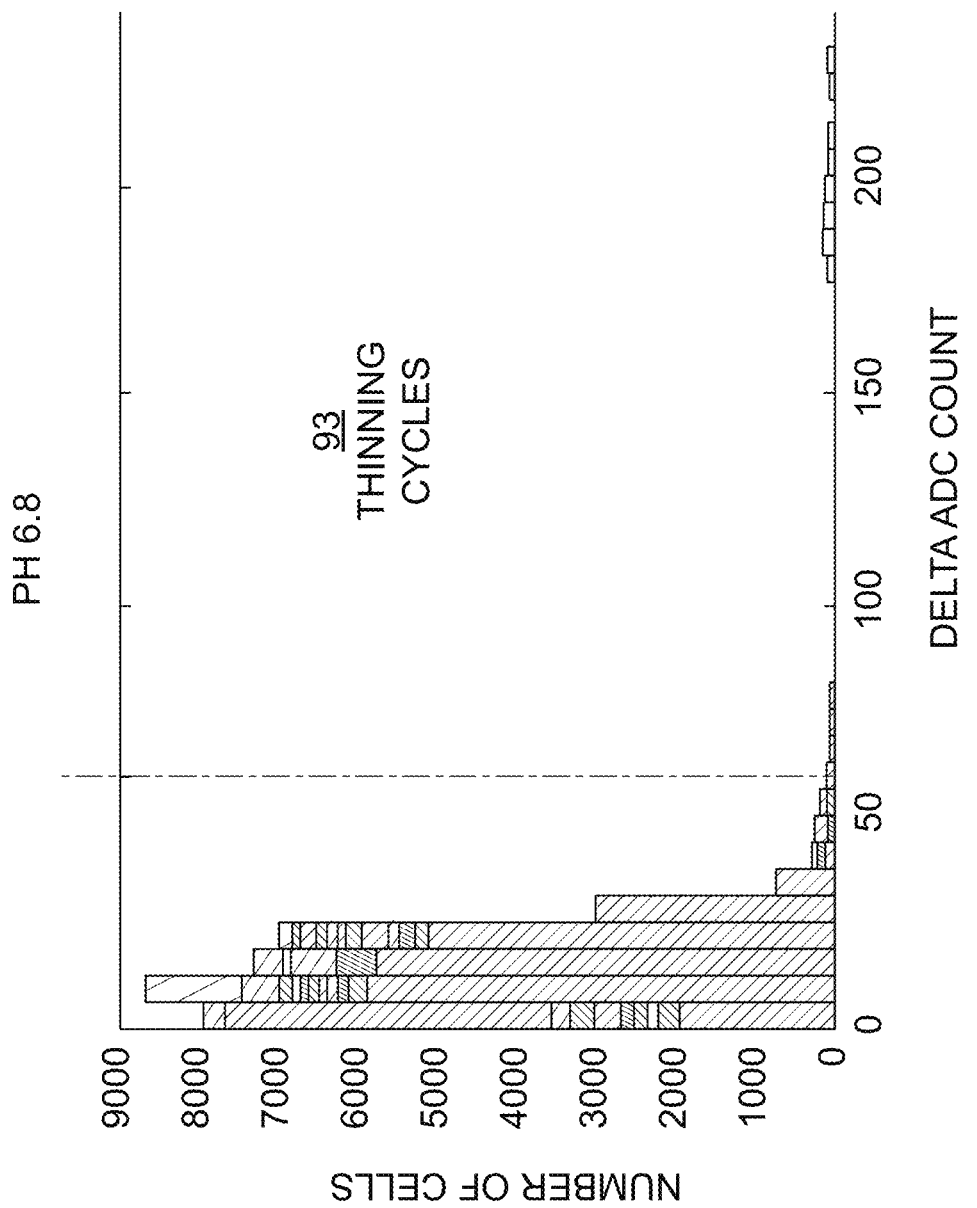

OSMOTIC IMBALANCE METHODS FOR BILAYER FORMATION

CROSS REFERENCE TO RELATED APPLICATIONS

This application is a continuation of U.S. patent application Ser. No. 16/219,464, filed Dec. 13, 2018, now U.S. Pat. No. 12,000,822, which is continuation of International Application No. PCT/EP2017/065626, filed Jun. 26, 2017, which claims priority to U.S. Provisional Application No. 62/355,140, filed Jun. 27, 2016, each of which is herein incorporated by reference in its entirety.

BACKGROUND OF THE INVENTION

Nanopore sequencing systems generally use a protein pore in a planar lipid bilayer (PLB) suspended over a well (e.g., a cylindrical well) containing an electrolyte solution, which is also present in a much larger exterior reservoir (e.g., above the well). A working electrode and reference electrode are used to apply an electrical bias across the well and the exterior reservoir. The PLB extends over the well to both electrically and physically seal the well and separates the well from the larger exterior reservoir. When a lipid solvent mixture is first deposited into the cells to form the lipid bilayers, lipid bilayers are spontaneously formed in some of the cells, but in other cells there is merely a thick lipid membrane with multiple layers of lipid molecules combined with the solvent spanning across each of the wells of the cells. In order to increase the yield of the nanopore based sequencing chip (i.e., the percentage of cells in the nanopore based sequencing chip with properly formed lipid bilayers and nanopores), the nanopore based sequencing chip may perform additional steps to facilitate the formation of lipid bilayers in additional cells. Therefore, improved techniques for forming lipid bilayers in the cells of a nanopore based sequencing chip would be desirable.

BRIEF DESCRIPTION OF THE DRAWINGS

Various embodiments of the invention are disclosed in the following detailed description and the accompanying drawings.

FIG. 16A is a histogram that illustrates that without the introduction of an osmotic imbalance between the salt buffer solution above and below the lipid membrane, salt buffer solution needs to be flowed many times (93 times) before the overall percentage of cells in the nanopore based sequencing chip with properly formed lipid bilayers (i.e., the yield of the nanopore based sequencing chip) is increased to an acceptable threshold.

DETAILED DESCRIPTION

The invention can be implemented in numerous ways, including as a process; a device, an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions through the nanopore can be observed. The size of the current is sensitive to the pore size.

A nanopore based sequencing chip may be used for nucleic acid (e.g., DNA) sequencing. A nanopore based sequencing chip incorporates a large number of sensor cells configured as an array. For example, an array of one million cells may include 1000 rows by 1000 columns of cells.

Figure 1:
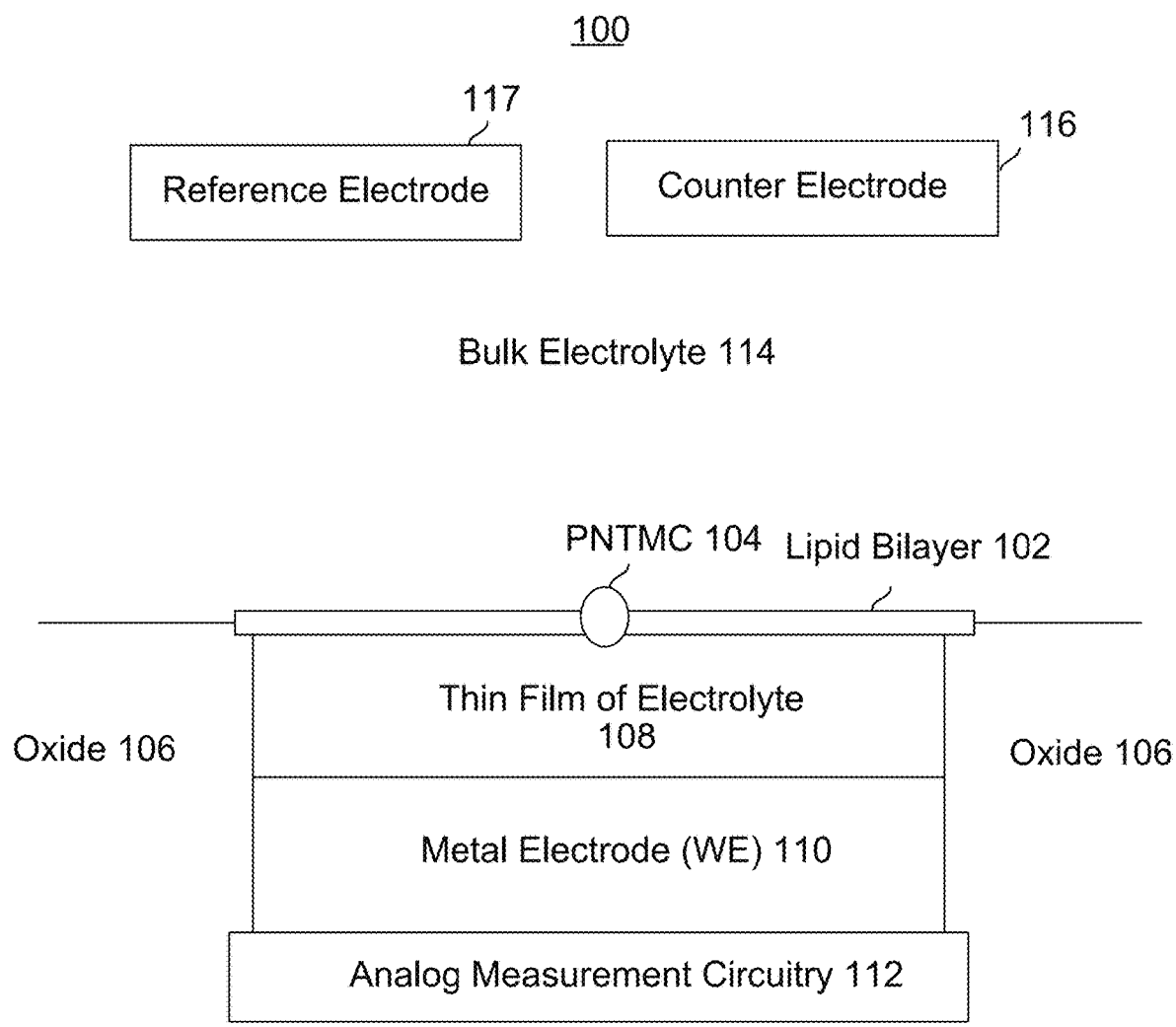
FIG. 1 illustrates an embodiment of a cell 100 in a nanopore based sequencing chip.

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing soluble protein nanopore transmembrane molecular complexes (PNTMC) and the analyte of interest is placed directly onto the surface of the cell. In one embodiment, a single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a volume of electrolyte 108. The volume of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is in electrical contact with the bulk electrolyte 114. The cell may also include a reference electrode 117.

Figure 2:
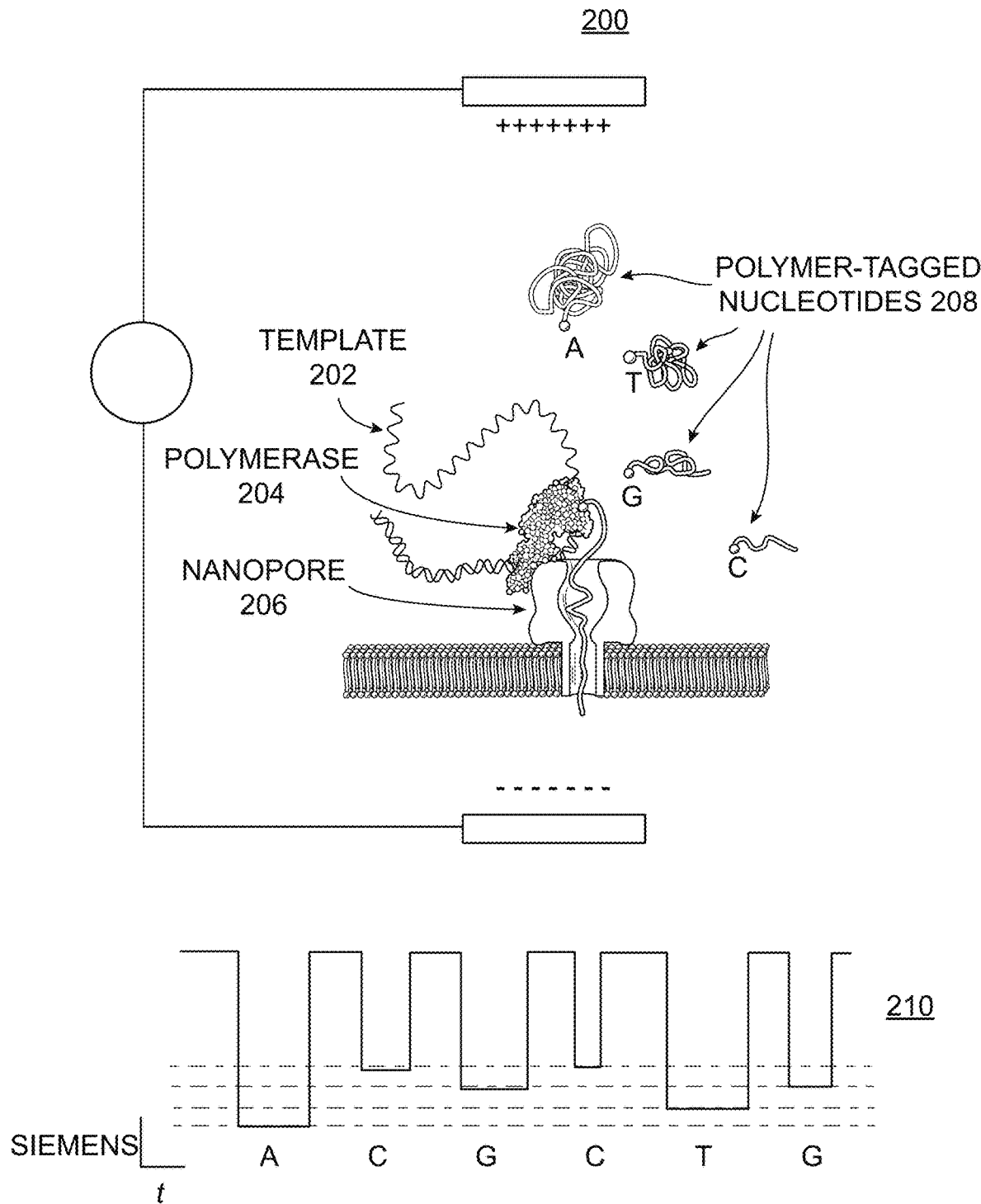
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
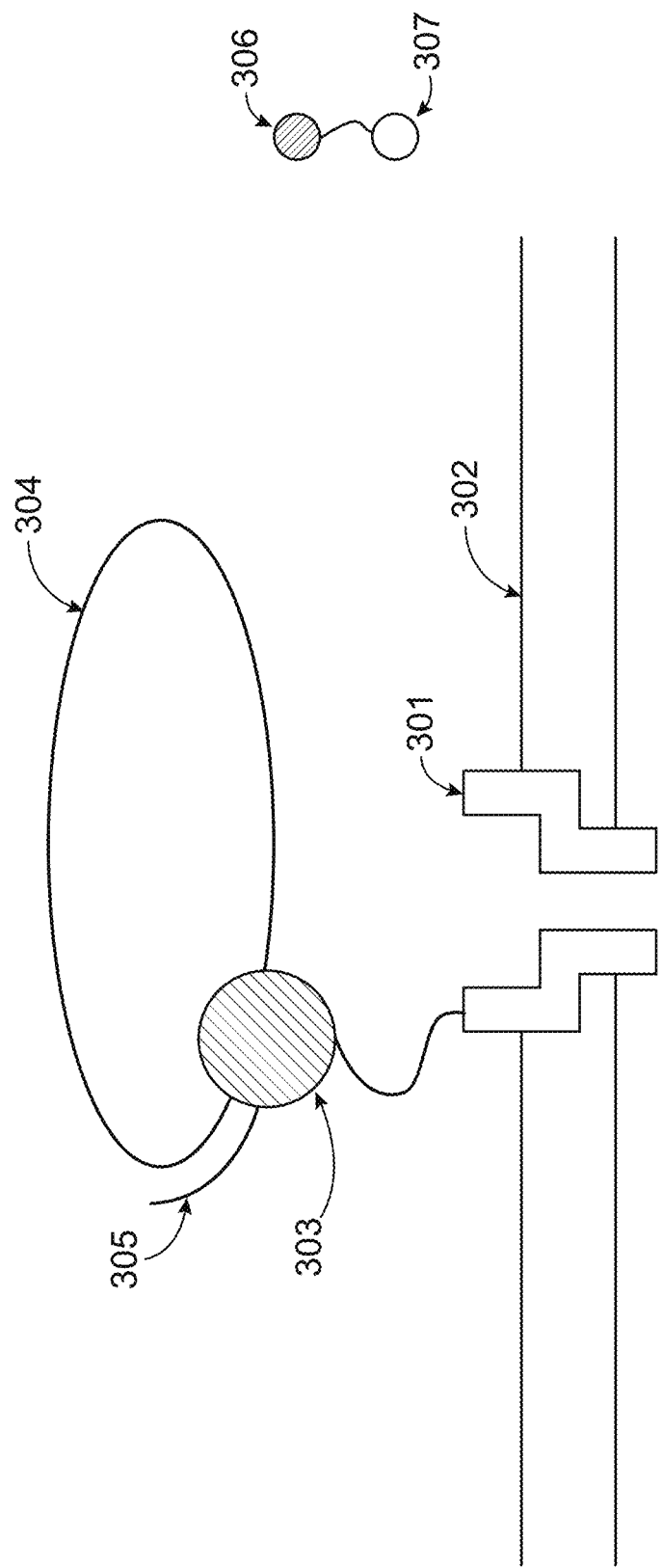
FIG. 3 illustrates an embodiment of a cell about to perform nucleotide sequencing with pre-loaded tags.
Figure 4C:
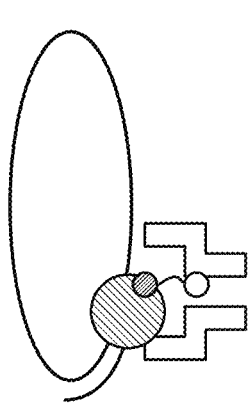
FIG. 4 illustrates an embodiment of a process 400 for nucleic acid sequencing with pre-loaded tags.
Figure 4D:
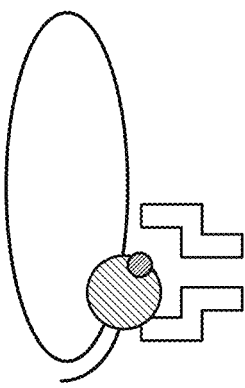
Figure 4B:
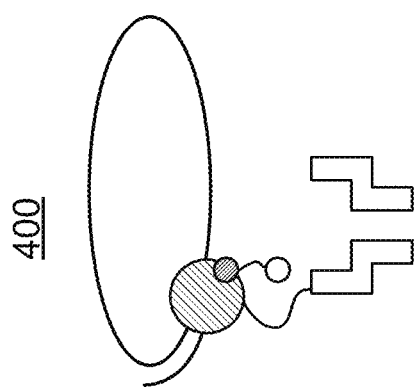
Figure 4E:
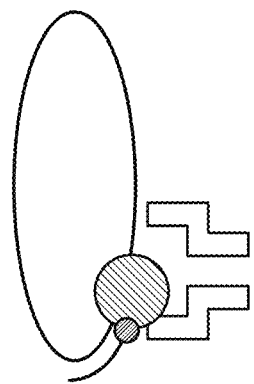
Figure 4A:
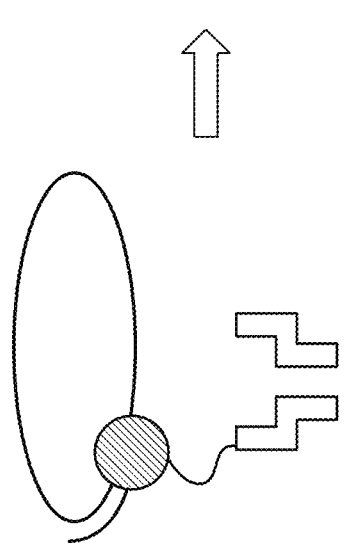
Figure 4F:
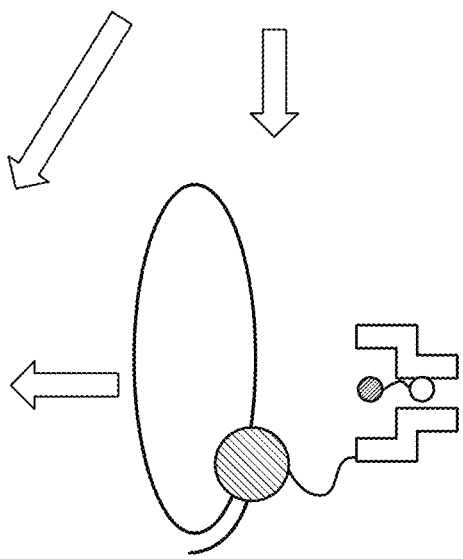

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 10,000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the conductance of the nanopore is ~300 picosiemens (300 pS). At stage C, the conductance of the nanopore is about 60 pS, 80 pS, 100 pS, or 120 pS, corresponding to one of the four types of tagged nucleotides respectively. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
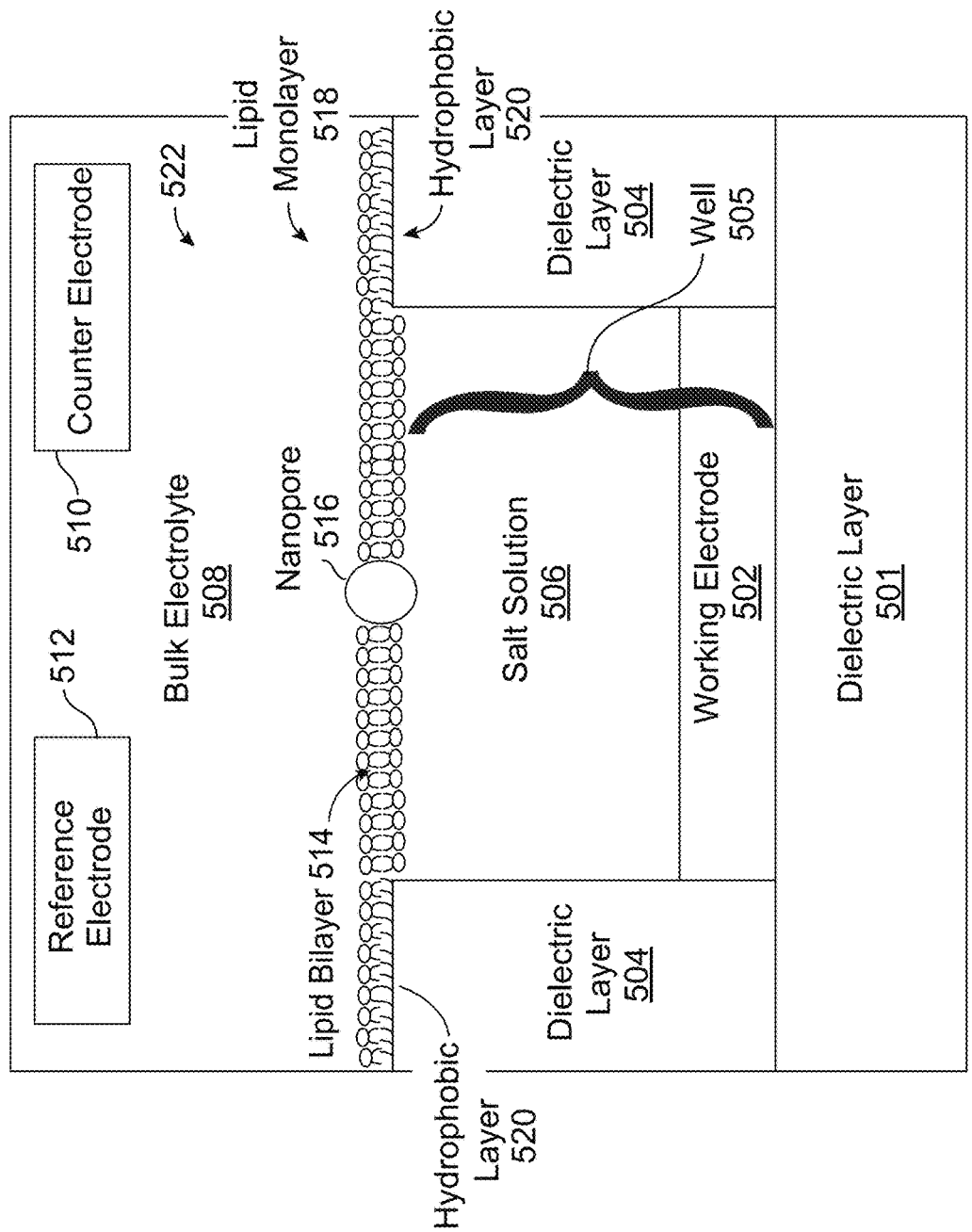
FIG. 5 illustrates an embodiment of a cell 500 in a nanopore based sequencing chip.

FIG. 5 illustrates an embodiment of a cell 500 in a nanopore based sequencing chip. Cell 500 includes a well 505 having two side walls and a bottom. In one embodiment, each side wall comprises a dielectric layer 504 and the bottom comprises a working electrode 502. In one embodiment, the working electrode 502 has a top side and a bottom side. In another embodiment, the top side of 502 makes up the bottom of the well 505 while the bottom side of 502 is in contact with dielectric layer 501. In another embodiment, the dielectric layer 504 is above dielectric layer 501. Dielectric layer 504 forms the walls surrounding a well 505 in which a working electrode 502 is located at the bottom. Suitable dielectric materials for use in the present invention (e.g., dielectric layer 501 or 504) include, without limitation, porcelain (ceramic), glass, mica, plastics, oxides, nitrides (e.g., silicon mononitride or SiN), silicon oxynitride, metal oxides, metal nitrides, metal silicates, transition-metal oxides, transition-metal nitrides, transition metal-silicates, oxynitrides of metals, metal aluminates, zirconium silicate, zirconium aluminate, hafnium oxide, insulating materials (e.g., polymers, epoxies, photoresist, and the like), or combinations thereof. Those of ordinary skill in the art will appreciate other dielectric materials that are suitable for use in the present invention.

In one aspect, cell 500 also includes one or more hydrophobic layers. As shown in FIG. 5, each dielectric layer 504 has a top surface. In one embodiment, the top surface of each dielectric layer 504 may comprise a hydrophobic layer. In one embodiment, silanization forms a hydrophobic layer 520 above the top surface of dielectric layer 504. For example, further silanization with silane molecules (i) containing 6 to 20 carbon-long chains (e.g., octadecyl-trichlorosilane, octadecyl-trimethoxysilane, or octadecyl-triethoxysilane), (ii) dimethyloctylchlorosilane (DMOC), or (iii) organofunctional alkoxysilane molecules (e.g., dimethylchloro-octadecyl-silane, methyldichloro-octadecyl-silane, trichloro-octadecyl-silane, trimethyl-octadecyl-silane, or triethyl-octadecyl-silane) can be done on the top surface of dielectric layer 504. In one embodiment, the hydrophobic layer is a silanized layer or silane layer. In one embodiment, the silane layer can be one molecule in thickness. In one aspect, dielectric layer 504 comprises a top surface suitable for adhesion of a membrane (e.g., a lipid bilayer comprising a nanopore). In one embodiment, the top surface suitable for adhesion of a membrane comprises a silane molecule as described herein. In some embodiments, hydrophobic layer 520 has a thickness provided in a nanometer (nM) or micrometer (m) scale. In other embodiments, the hydrophobic layer may extend down along all or a part of the dielectric layer 504. (see also Davis et al. U.S. 20140034497, which is incorporated herein by reference in its entirety).

In another aspect, well 505 (formed by the dielectric layer walls 504) further includes a volume of salt solution 506 above working electrode 502. In general, the methods of the present invention comprise the use of a solution (e.g., a salt solution, salt buffer solution, electrolyte, electrolyte solution, or bulk electrolyte) that comprises osmolytes. As used herein, the term "osmolyte" refers to any soluble compound that when dissolved into solution increases the osmolarity of that solution. In the present invention, an osmolyte is a compound that is soluble in solution within the architecture of a nanopore sequencing system, e.g., a well containing a salt solution or a bulk electrolyte as described herein. As such, the osmolytes of the present invention affect osmosis, particularly osmosis across a lipid bilayer. Osmolytes for use in the present invention include, without limitation, ionic salts such as lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$); polyols and sugars such as glycerol, erythritol, arabitol, sorbitol, mannitol, xylitol, mannisidomannitol, glycosyl glycerol, glucose, fructose, sucrose, trehalose, and isofluoroside; polymers such as dextrans, levans, and polyethylene glycol; and some amino acids and derivatives thereof such as glycine, alanine, alpha-alanine, arginine, proline, taurine, betaine, octopine, glutamate, sarcosine, y-aminobutyric acid, and trimethylamine N-oxide ("TMAO") (see also e.g., Fisher et al. U.S. 20110053795, incorporated herein by reference in its entirety). In one embodiment, the present invention utilizes a solution comprising an osmolyte, wherein the osmolyte is an ionic salt. Those of ordinary skill in the art will appreciate other compounds that are suitable osmolytes for use in the present invention. In another aspect, the present invention provides solutions comprising two or more different osmolytes.

The architecture of the nanopore based sequencing chip described herein comprises an array of wells (e.g., FIG. 5) having various volume capacities, including nanoliter (nL), picoliter (pL), femtoliter (fL), attoliter (aL), zeptoliter (zL) and yocoliter (yL) capacities. For example, the volume of electrolyte 108 (e.g., FIG. 1) or salt solution 506 (e.g., FIG. 5) is provided in a nL, pL, fL, aL, zL, or yL scale. In one embodiment of the present invention, the volume of the electrolyte or salt solution formed by the wells (e.g., well 505 in FIG. 5) of the present invention, or the volume of electrolyte or salt solution used in methods described herein may be provided in a nanoliter (nL), picoliter (pL), femtoliter (fL), attoliter (aL), zeptoliter (zL), or yocoliter (yL) scale. The wells may alternately be described by their volume in cubic micrometers, or similar dimensions, rather than by volume. It will be within the ability of one skilled in the art to determine the necessary conversion between units, for example from cubic micrometers to picoliters, femtoliters, or the like.

As shown in FIG. 5, a membrane is formed on the top surfaces of dielectric layer 504 and spans across well 505. For example, the membrane includes a lipid monolayer 518 formed on top of hydrophobic layer 520. As the membrane reaches the opening of well 505, the lipid monolayer transitions to a lipid bilayer 514 that spans across the opening of the well. The lipid monolayer 518 may also extend along all or a part of the vertical surface (i.e., side wall) of a dielectric layer 504. In one embodiment, the vertical surface 504 along which the monolayer 518 extends comprises a hydrophobic layer. A bulk electrolyte 508 containing protein nanopore transmembrane molecular complexes (PNTMC) and the analyte of interest is placed directly above the well. A single PNTMC/nanopore 516 is inserted into lipid bilayer 514. In one embodiment, insertion into the bilayer is by electroporation. Nanopore 516 crosses lipid bilayer 514 and provides the only path for ionic flow from bulk electrolyte 508 to working electrode 502.

Cell 500 includes a counter electrode (CE) 510, which is in electrical contact with the bulk electrolyte 508. Cell 500 may optionally include a reference electrode 512. In some embodiments, counter electrode 510 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

In some embodiments, working electrode 502 is a metal electrode. For non-faradaic conduction, working electrode 502 may be made of metals that are resistant to corrosion and oxidation, e.g., platinum, gold, titanium nitride and graphite. For example, working electrode 502 may be a platinum electrode with electroplated platinum. In another example, working electrode 502 may be a titanium nitride (TiN) working electrode.

As shown in FIG. 5, nanopore 516 is inserted into the planar lipid bilayer 514 suspended over well 505. An electrolyte solution is present both inside well 505, i.e., trans side, (see salt solution 506) and in a much larger external reservoir 522, i.e., cis side, (see bulk electrolyte 508). The bulk electrolyte 508 in external reservoir 522 is above multiple wells of the nanopore based sequencing chip. Lipid bilayer 514 extends over well 505 and transitions to lipid monolayer 518 where the monolayer is attached to hydrophobic layer 520. This geometry both electrically and physically seals well 505 and separates the well from the larger external reservoir. While neutral molecules, such as water and dissolved gases, may pass through lipid bilayer 514, ions may not. Nanopore 516 in lipid bilayer 514 provides a single path for ions to be conducted into and out of well 505.

For nucleic acid sequencing, a polymerase is attached to nanopore 516. A template of nucleic acid (e.g., DNA) is held by the polymerase. For example, the polymerase synthesizes DNA by incorporating hexaphosphate mono-nucleotides (HMN) from solution that are complementary to the template. A unique, polymeric tag is attached to each HMN. During incorporation, the tag threads the nanopore aided by an electric field gradient produced by the voltage between counter electrode 510 and working electrode 502. The tag partially blocks nanopore 516, procuring a measurable change in the ionic current through nanopore 516. In some embodiments, an alternating current (AC) bias or direct current (DC) voltage is applied between the electrodes.

The step of inserting a nanopore into a lipid bilayer is performed after it is determined that a lipid bilayer has been properly formed within a cell of the nanopore based sequencing chip. In some techniques, the process of determining whether a lipid bilayer has been properly formed in a cell may cause an already properly formed lipid bilayer to be destroyed. For example, a stimulus voltage may be applied to cause a current to flow across the electrodes. Although the measured response to the stimulus voltage may be used to distinguish between a cell with a properly formed lipid bilayer (i.e., a lipid bilayer that is two layers of lipid molecules thick) from a cell without a properly formed lipid bilayer (e.g., a cell with a thick lipid and solvent combined film that spans across the well of the cell), the stimulus voltage level is high enough to cause an already properly formed lipid bilayer to break down in some instances. In other words, the stimulus voltage for testing the lipid bilayer may be destructive to the lipid bilayer. In the event that an already properly formed lipid bilayer is destroyed by the stimulus voltage, a very high current begins to flow across the electrodes as a result of the short-circuit condition. In response, the system may try to reform a new lipid bilayer in the particular cell again; however, this is both time-consuming and inefficient. In addition, a lipid bilayer may not reform in the particular cell in a subsequent trial. As a result, the overall percentage of cells in the nanopore based sequencing chip with properly formed lipid bilayers and nanopores (i.e., the yield of the nanopore based sequencing chip) is reduced.

A non-destructive technique to detect a lipid bilayer formed in a cell of a nanopore based sequencing chip is disclosed. A non-destructive technique to detect a lipid bilayer has many advantages, including increasing the efficiency and yield of the nanopore based sequencing chip.

Figure 6A:
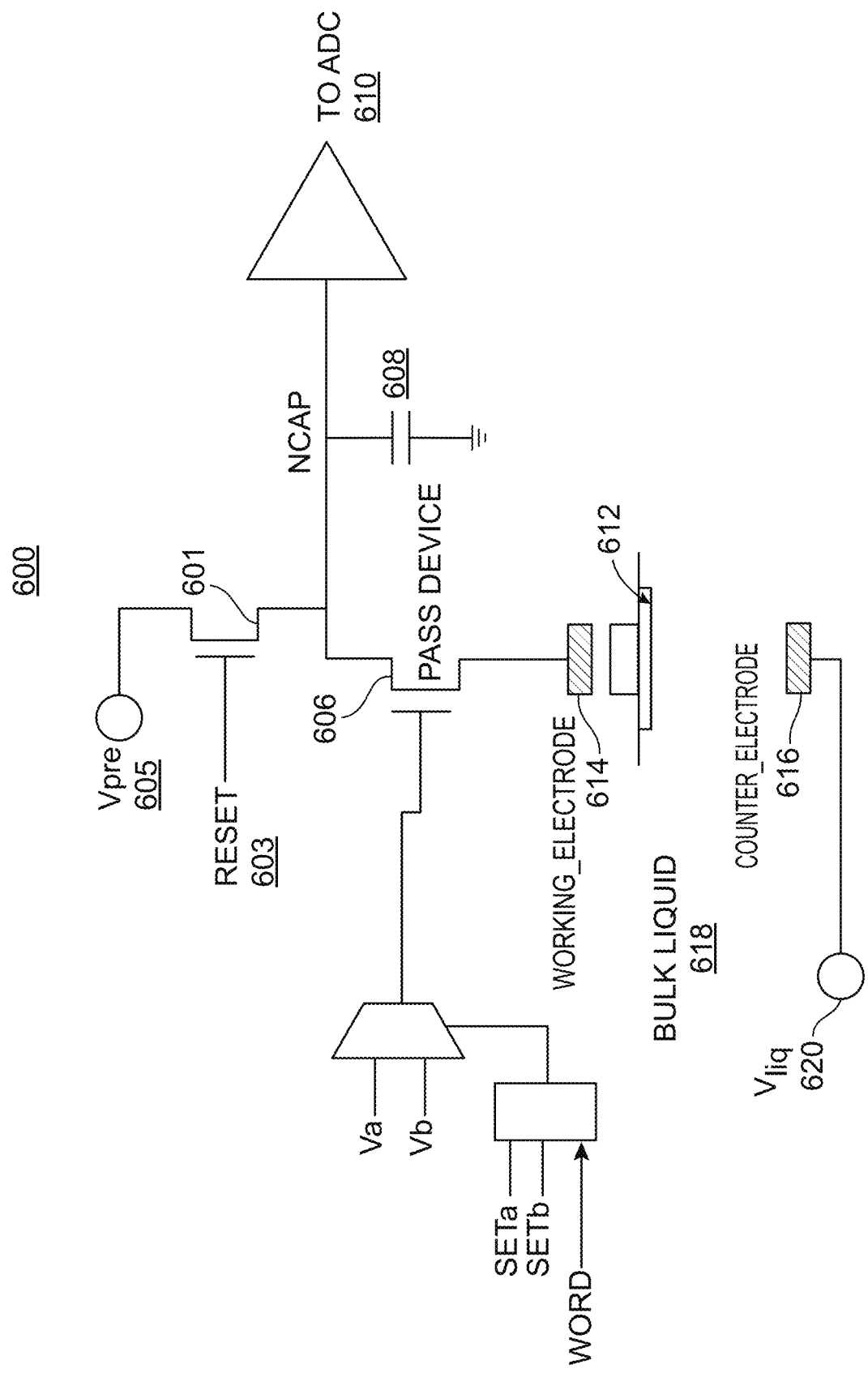
FIG. 6A illustrates an embodiment of a circuitry 600 in a cell of a nanopore based sequencing chip, wherein the circuitry can be configured to detect whether a lipid bilayer is formed in the cell without causing an already formed lipid bilayer to break down.

FIG. 6A illustrates an embodiment of a circuitry 600 in a cell of a nanopore based sequencing chip wherein the circuitry can be configured to detect whether a lipid bilayer is formed in the cell without causing an already formed lipid bilayer to break down.

FIG. 6A shows a lipid membrane or lipid bilayer 612 situated between a cell working electrode 614 and a counter electrode 616, such that a voltage is applied across lipid membrane/bilayer 612. A lipid bilayer is a thin membrane made of two layers of lipid molecules. A lipid membrane is a membrane made of several layers (more than two) of lipid molecules. Lipid membrane/bilayer 612 is also in contact with a bulk liquid/electrolyte 618. Note that working electrode 614, lipid membrane/bilayer 612, and counter electrode 616 are drawn upside down as compared to the working electrode, lipid bilayer, and counter electrode in FIG. 1. In some embodiments, the counter electrode is shared between a plurality of cells, and is therefore also referred to as a common electrode. The common electrode can be configured to apply a common potential to the bulk liquid in contact with the lipid membranes/bilayers in the measurements cells by connecting the common electrode to a voltage source $V_{liq}$ 620. The common potential and the common electrode are common to all of the measurement cells. There is a working cell electrode within each measurement cell; in contrast to the common electrode, working cell electrode 614 is configurable to apply a distinct potential that is independent from the working cell electrodes in other measurement cells.

Figure 6B:
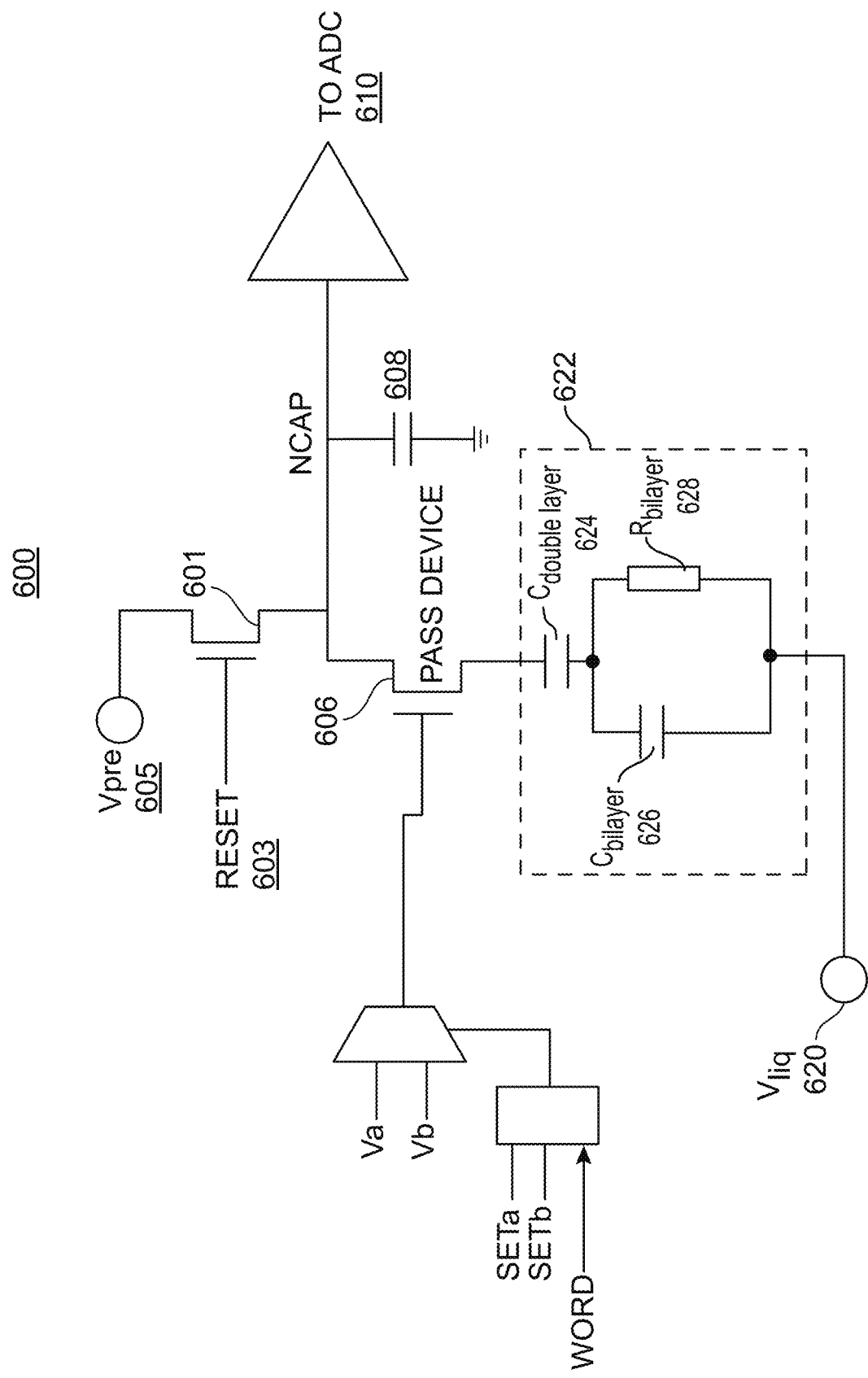
FIG. 6B illustrates the same circuitry 600 in a cell of a nanopore based sequencing chip as that shown in FIG. 6A. Comparing to FIG. 6A, instead of showing a lipid membrane/bilayer between the working electrode and the counter electrode, an electrical model representing the electrical properties of the working electrode and the lipid membrane/bilayer is shown.

FIG. 6B illustrates the same circuitry 600 in a cell of a nanopore based sequencing chip as that shown in FIG. 6A. Comparing to FIG. 6A, instead of showing a lipid membrane/bilayer between the working electrode and the counter electrode, an electrical model representing the electrical properties of the working electrode and the lipid membrane/bilayer is shown.

Electrical model 622 includes a capacitor 624 representing the electrical properties of working electrode 614. The capacitance associated with working electrode 614 is also referred to as a double layer capacitance ($C_{double\ layer}$). Electrical model 622 further includes a capacitor 626 ($C_{bilayer}$) that models a capacitance associated with the lipid membrane/bilayer and a resistor 628 ($R_{bilayer}$) that models a resistance associated with the lipid membrane/bilayer. The resistance associated with the lipid membrane/bilayer is very high, and therefore $R_{bilayer}$ may be replaced by an open circuit, which reduces electrical model 622 to $C_{double\ layer}$ in series with $C_{bilayer}$.

Voltage source $V_{liq}$ 620 is an alternating current (AC) voltage source. Counter electrode 616 is immersed in the bulk liquid 618, and an AC non-Faradaic mode is utilized to modulate a square wave voltage $V_{liq}$ and apply it to the bulk liquid in contact with the lipid membranes/bilayers in the measurement cells. In some embodiments, $V_{liq}$ is a square wave with a magnitude of ±200-250 mV and a frequency between 25 and 100 Hz.

Pass device 606 is a switch that can be used to connect or disconnect the lipid membrane/bilayer and the electrodes from the measurement circuitry 600. The switch enables or disables a voltage stimulus that can be applied across the lipid membrane/bilayer in the cell. Before lipids are deposited to the cell to form a lipid bilayer, the impedance between the two electrodes is very low because the well of the cell is not sealed, and therefore switch 606 is kept open to avoid a short-circuit condition. Switch 606 may be closed once lipid solvent has been deposited to the cell that seals the well of the cell.

Circuitry 600 further includes an on-chip fabricated integrating capacitor 608 ($n_{cap}$). Integrating capacitor 608 is pre-charged by using a reset signal 603 to close switch 601, such that integrating capacitor 608 is connected to a voltage source $V_{pre}$ 605. In some embodiments, voltage source $V_{pre}$ 605 provides a constant positive voltage with a magnitude of 900 mV. When switch 601 is closed, integrating capacitor 608 is pre-charged to the positive voltage level of voltage source $V_{pre}$ 605.

After integrating capacitor 608 is pre-charged, reset signal 603 is used to open switch 601 such that integrating capacitor 608 is disconnected from voltage source $V_{pre}$ 605. At this point, depending on the level of $V_{liq}$, the potential of counter electrode 616 may be at a higher level than the potential of working electrode 614, or vice versa. For example, during the positive phase of square wave $V_{liq}$ (i.e., the dark period of the AC voltage source signal cycle), the potential of counter electrode 616 is at a higher level than the potential of working electrode 614. Similarly, during the negative phase of square wave $V_{liq}$ (i.e., the bright period of the AC voltage source signal cycle), the potential of counter electrode 616 is at a lower level than the potential of working electrode 614. Due to this potential difference, integrating capacitor 608 may be charged during the dark period of the AC voltage source signal cycle and discharged during the bright period of the AC voltage source signal cycle.

Depending on the sampling rate of an analog-to-digital converter (ADC) 610, integrating capacitor 608 charges or discharges for a fixed period of time, and then the voltage stored in integrating capacitor 608 may be read out by ADC 610. After the sampling by ADC 610, integrating capacitor 608 is pre-charged again by using reset signal 603 to close switch 601, such that integrating capacitor 608 is connected to voltage source $V_{pre}$ 605 again. In some embodiments, the sampling rate of ADC 610 is between 1500 to 2000 Hz. In some embodiments, the sampling rate of ADC 610 is up to 5 kHz. For example, with a sampling rate of 1 kHz, integrating capacitor 608 charges or discharges for a period of ~1 ms, and then the voltage stored in integrating capacitor 608 is read out by ADC 610. After the sampling by ADC 610, integrating capacitor 608 is pre-charged again by using reset signal 603 to close switch 601 such that integrating capacitor 608 is connected to voltage source $V_{pre}$ 605 again. The steps of pre-charging the integrating capacitor 608, waiting a fixed period of time for the integrating capacitor 608 to charge or discharge, and sampling the voltage stored in integrating capacitor by ADC 610 are then repeated in cycles throughout a lipid bilayer measurement phase of the system.

Circuitry 600 may be used to detect whether a lipid bilayer is formed in the cell by monitoring a delta voltage change, $\Delta V_{ADC}$, at integrating capacitor 608 ($n_{cap}$) in response to a delta voltage change ($\Delta V_{liq}$) applied to the bulk liquid in contact with the lipid membrane/bilayer. As will be described in greater detail below, during the lipid bilayer measurement phase, circuitry 600 may be modeled as a voltage divider with $C_{bilayer}$ 626, $C_{double\ layer}$ 624, and $n_{cap}$ 608 connected in series, and a voltage change tapped at an intermediate point of the voltage divider can be read by ADC 610 for determining whether a lipid bilayer has been formed.

Figure 7:
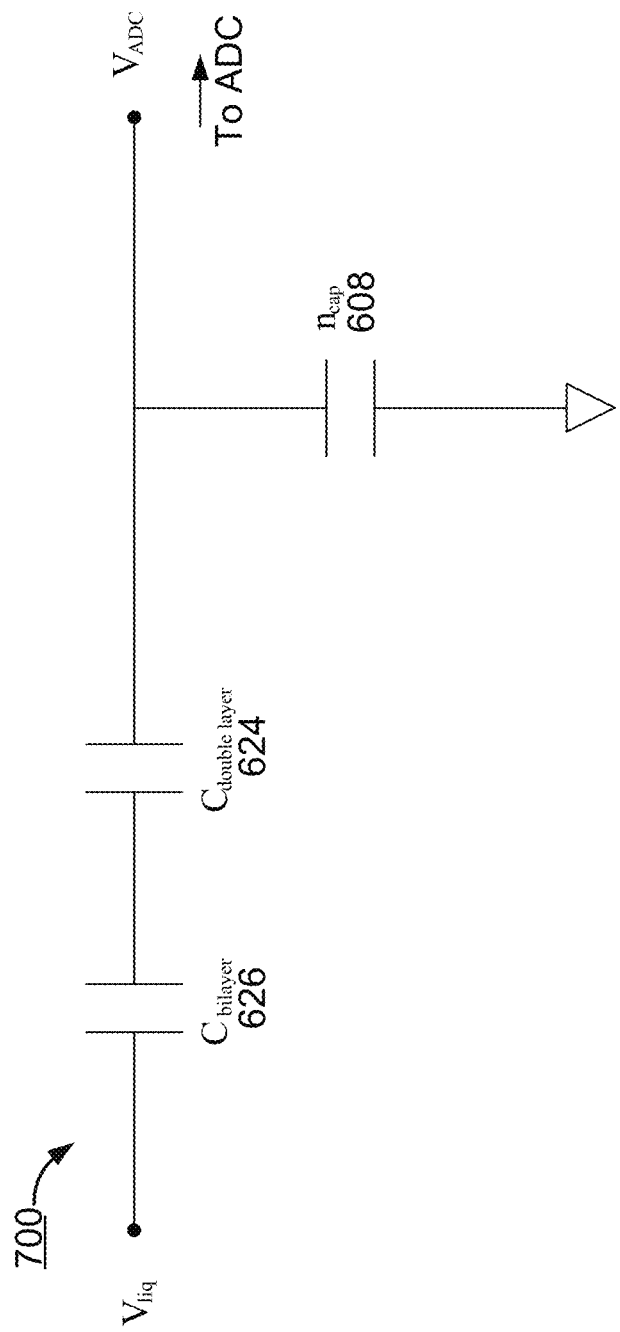
FIG. 7 illustrates an electrical model 700 representing the electrical properties of a portion of circuitry 600 during the lipid bilayer measurement phase of the system.

FIG. 7 illustrates an electrical model 700 representing the electrical properties of a portion of circuitry 600 during the lipid bilayer measurement phase of the system. As shown in FIG. 7, $C_{double\ layer}$ 624 is connected in series with $C_{bilayer}$ 626, but $R_{bilayer}$ 628 (see FIG. 6B) is eliminated from electrical model 700. $R_{bilayer}$ 628 can be removed from electrical model 700 because the resistance associated with the lipid membrane/bilayer is very high, and therefore $R_{bilayer}$ may be approximated as an open circuit. As shown in FIG. 7, $C_{double\ layer}$ 624 and $C_{bilayer}$ 626 are further connected in series with $n_{cap}$ 608.

When operating in an AC mode, the voltage read by the ADC ($V_{ADC}$) can be determined by:

$$V_{ADC} = V_{liq} * \frac{Z(n\text{cap})}{Z(\text{bilayer}) + Z(\text{double layer}) + Z(n\text{cap})} \quad \text{Equation (1)}$$

where $Z=1/(j\omega C)$,

Z(ncap) is the AC impedance associated with $n_{cap}$,

Z(double layer) is the AC impedance associated with the working electrode, and Z(bilayer) is the AC impedance associated with the lipid membrane/bilayer.

The AC impedance of the double layer, Z(double layer), has a very low value compared to Z(bilayer) and Z(ncap) because $C_{double\ layer}$ is much larger than $C_{bilayer}$ or the capacitance of $n_{cap}$. Therefore, substituting $Z(n\text{cap})=1/(j\omega C_{ncap})$, $Z(\text{bilayer})=1/j\omega C_{bilayer}$, and $Z(\text{double layer})=0$, equation (1) can be simplified as:

$$V_{ADC} = V_{liq} * \frac{C(\text{bilayer})}{C(n\text{cap}) + C(\text{bilayer})} \quad \text{Equation (2)}$$

where C(ncap) is the capacitance associated with $n_{cap}$, and C(bilayer) is the capacitance associated with the lipid membrane/bilayer.

When lipids are first deposited into the cells to form the lipid bilayers, some of the cells have lipid bilayers spontaneously formed, but some of the cells merely have a thick lipid membrane (with multiple layers of lipid molecules and solvent combined together) spanning across each of the wells of the cells. The capacitance associated with a lipid bilayer is larger than the capacitance associated with a lipid membrane that is more than two layers of lipid molecules thick because the capacitance of the lipid membrane/bilayer is inversely proportional to its thickness. As a lipid membrane thins out and transitions to become a lipid bilayer, the thickness decreases and its associated capacitance increases.

In Equation (2) above, as a lipid bilayer begins to form within a cell, C(bilayer) increases while C(ncap) remains constant, such that on the whole $V_{ADC}$ increases. An increase in $V_{ADC}$ can therefore be used as an indicator that a lipid bilayer has been formed within a cell.

In some embodiments, a delta voltage change $\Delta V_{ADC}$ at integrating capacitor 608 ($n_{cap}$) in response to a delta voltage change ($\Delta V_{liq}$) applied to the bulk liquid in contact with the lipid membrane/bilayer is monitored in order to detect whether a lipid bilayer has been formed in a cell. For example, Equation (2) may be rewritten as:

$$\Delta V_{ADC} = \Delta V_{liq} * \frac{C(\text{bilayer})}{C(n\text{cap}) + C(\text{bilayer})} \quad \text{Equation (3)}$$

where $\Delta V_{ADC}$ is a voltage change at integrating capacitor 608 ($n_{cap}$) read by the ADC,
$\Delta V_{liq}$ is a voltage change applied to the bulk liquid,
C(ncap) is the capacitance associated with $n_{cap}$,
and C(bilayer) is the capacitance associated with the lipid membrane/bilayer.

In Equation (3) above, because C(ncap) remains constant, while C(bilayer) increases as a lipid bilayer begins to form within a cell, $\Delta V_{ADC}$ increases as well. $\Delta V_{ADC}$ is roughly proportional to the capacitance associated with the lipid membrane/bilayer, C(bilayer). An increase in $\Delta V_{ADC}$ can therefore be used as an indicator that a lipid bilayer has been formed within a cell.

In some embodiments, in order to maximize the observable $\Delta V_{ADC}$ for a more reliable detection of a lipid bilayer, $\Delta V_{ADC}$ in response to a maximum voltage change applied to the bulk liquid in contact with the lipid membrane/bilayer (max $\Delta V_{liq}$) is monitored in order to detect whether a lipid bilayer has been formed in a cell.

Figures 8A, 8B:
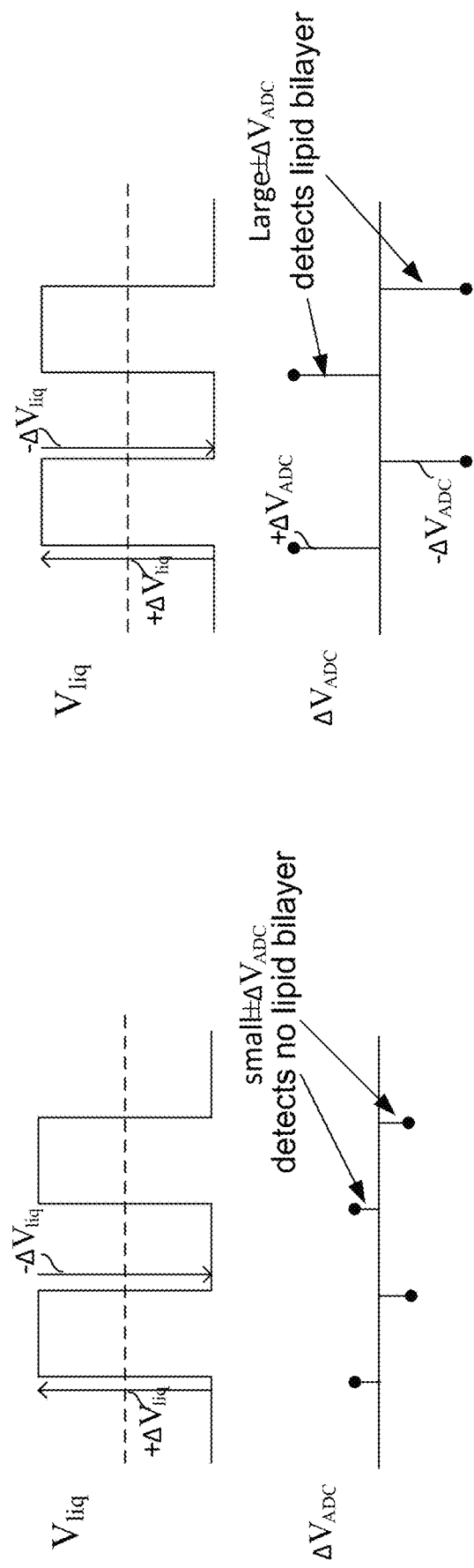
FIG. 8A illustrates that a small observed $\pm \Delta V_{ADC}$ in response to a $\pm \Delta V_{liq}$ detects that no lipid bilayer has been formed in the cell.
FIG. 8B illustrates that a large observed $\pm \Delta V_{ADC}$ in response to a $\pm \Delta V_{liq}$ detects that a lipid bilayer has been formed in a cell.

FIG. 8A illustrates that a small observed positive/negative voltage change $\pm \Delta V_{ADC}$ in response to a positive/negative voltage change $\pm \Delta V_{liq}$ results in no lipid bilayer being detected to have been formed in the cell. FIG. 8B illustrates that a large observed positive/negative voltage change $\pm \Delta V_{ADC}$ in response to a positive/negative voltage change $\pm \Delta V_{liq}$ results in the detection of a lipid bilayer having been formed in a cell.

In FIG. 8A, a maximum positive voltage change $+\Delta V_{liq}$ occurs when the square wave $V_{liq}$ changes from a negative phase to a positive phase, while a maximum negative voltage change $-\Delta V_{liq}$ occurs when the square wave $V_{liq}$ changes from a positive phase to a negative phase. In FIG. 8A, at the instance when $\Delta V_{liq}$ is at a positive maximum, only a small $+\Delta V_{ADC}$ can be observed if a lipid bilayer has not been formed in the cell; at the instance when $\Delta V_{liq}$ is at a negative maximum, only a small $-\Delta V_A DC$ can be observed if a lipid bilayer has not been formed in the cell.

In FIG. 8B, at the instance when $\Delta V_{liq}$ is at a positive maximum, a large positive voltage change $+\Delta V_{ADC}$ can be observed if a lipid bilayer has already been formed in the cell. And at the instance when $\Delta V_{liq}$ is at a negative maximum, a large negative voltage change $-\Delta V_{ADC}$ can be observed if a lipid bilayer has already been formed in the cell.

In some embodiments, the absolute value of $\Delta V_{ADC}$ ($|\Delta V_{ADC}|$) observed when the absolute value of $\Delta V_{liq}$ ($|\Delta V_{liq}|$) is at a maximum is compared with a predetermined threshold. If ($|\Delta V_{ADC}|$>predetermined threshold), then it is determined that a lipid bilayer is detected. Conversely, if ($|\Delta V_{ADC}|$<predetermined threshold), then it is determined that a lipid bilayer is not detected.

Figure 9A:
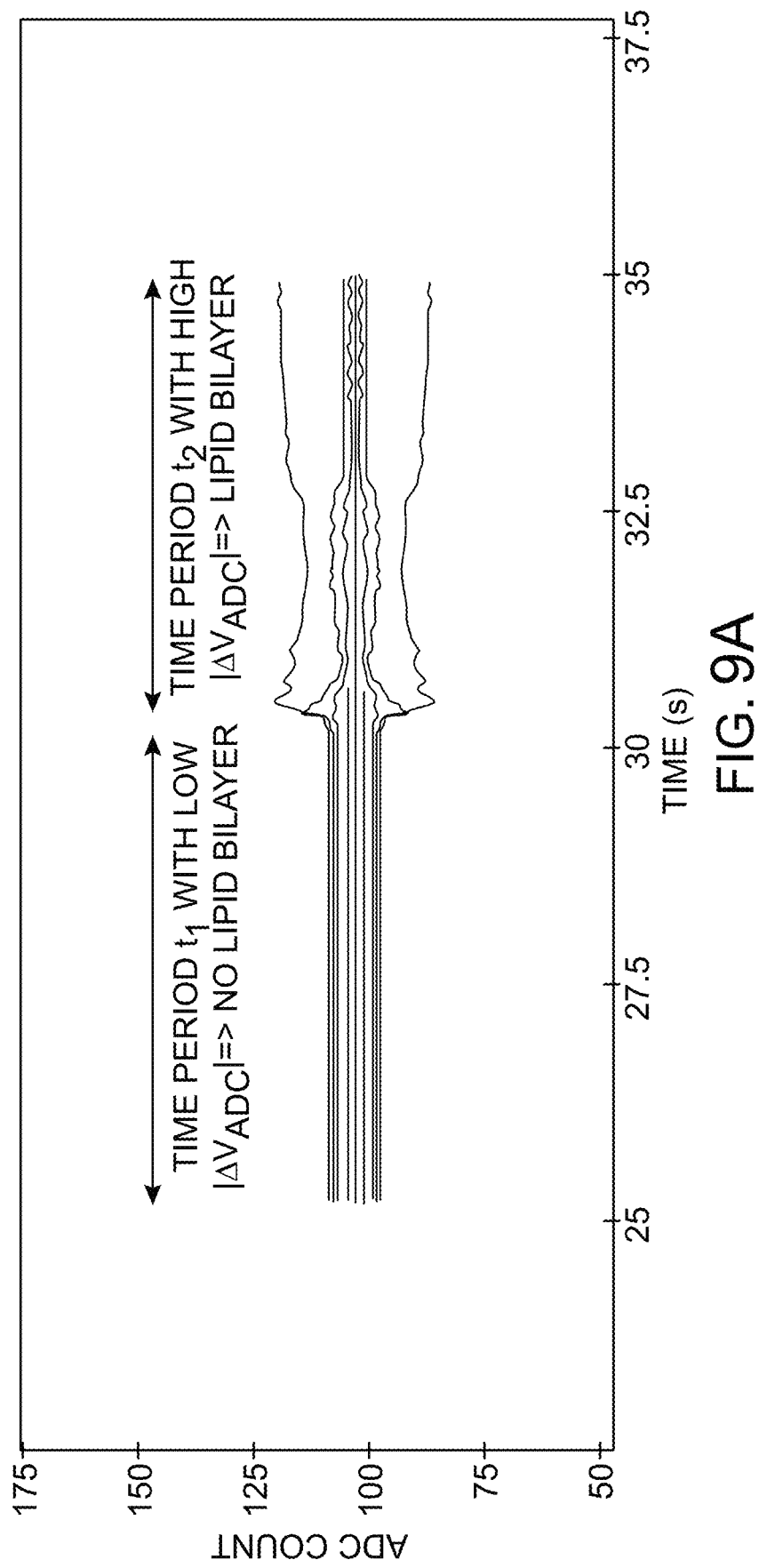
FIG. 9A illustrates an exemplary plot of $V_{ADC}$ versus time before and after a lipid bilayer is formed within a cell.

FIG. 9A illustrates an exemplary plot of $V_{ADC}$ versus time before and after a lipid bilayer is formed within a cell. The plot in FIG. 9A is based on real testing data. As shown in FIG. 9A, the units of $V_{ADC}$ on the y-axis are in ADC counts. However, other units may be used as well. As shown in FIG. 9A, during a time period $t_1$ when a lipid bilayer has not been formed, the recorded $|\Delta V_{ADC}|$ values are smaller than those recorded during a time period $t_2$ after a lipid bilayer has been formed in the cell.

Figure 9B:
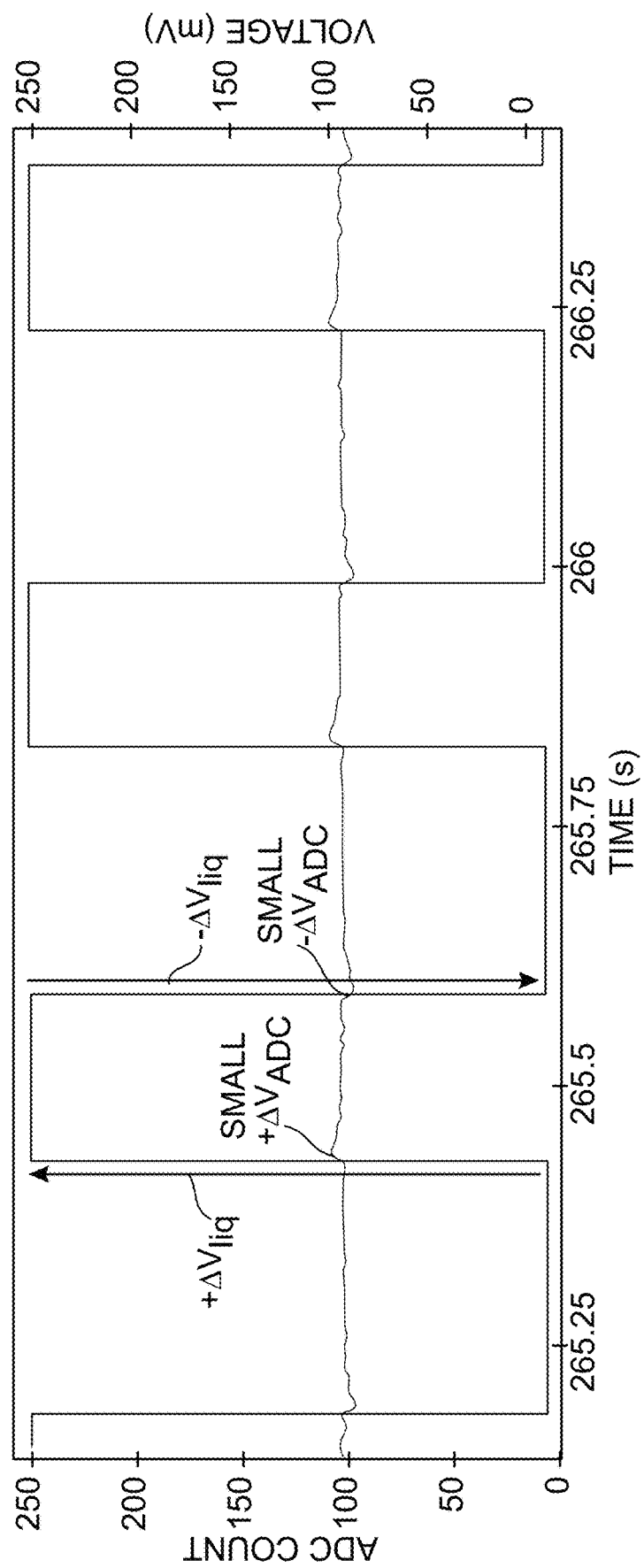
FIG. 9B illustrates a zoomed-in view of the exemplary plot of $V_{ADC}$ versus time (see FIG. 9A) during the time period $t_1$ when a lipid bilayer has not been formed.

FIG. 9B illustrates a zoomed-in view of the exemplary plot of $V_{ADC}$ versus time (see FIG. 9A) during the time period $t_1$ when a lipid bilayer has not been formed. The results shown in FIG. 9B are consistent with FIG. 8A. In FIG. 9B, a maximum $+\Delta V_{liq}$ occurs when the square wave $V_{liq}$ changes from a negative phase to a positive phase, while a maximum $-\Delta V_{liq}$ occurs when the square wave $V_{liq}$ changes from a positive phase to a negative phase. In FIG. 9B, at the instance when $\Delta V_{liq}$ is at a positive maximum, only a small $+\Delta V_{ADC}$ can be observed because a lipid bilayer has not been formed in the cell; at the instance when $\Delta V_{liq}$ is at a negative maximum, only a small $-\Delta V_{ADC}$ can be observed because a lipid bilayer has not been formed in the cell.

Figure 9C:
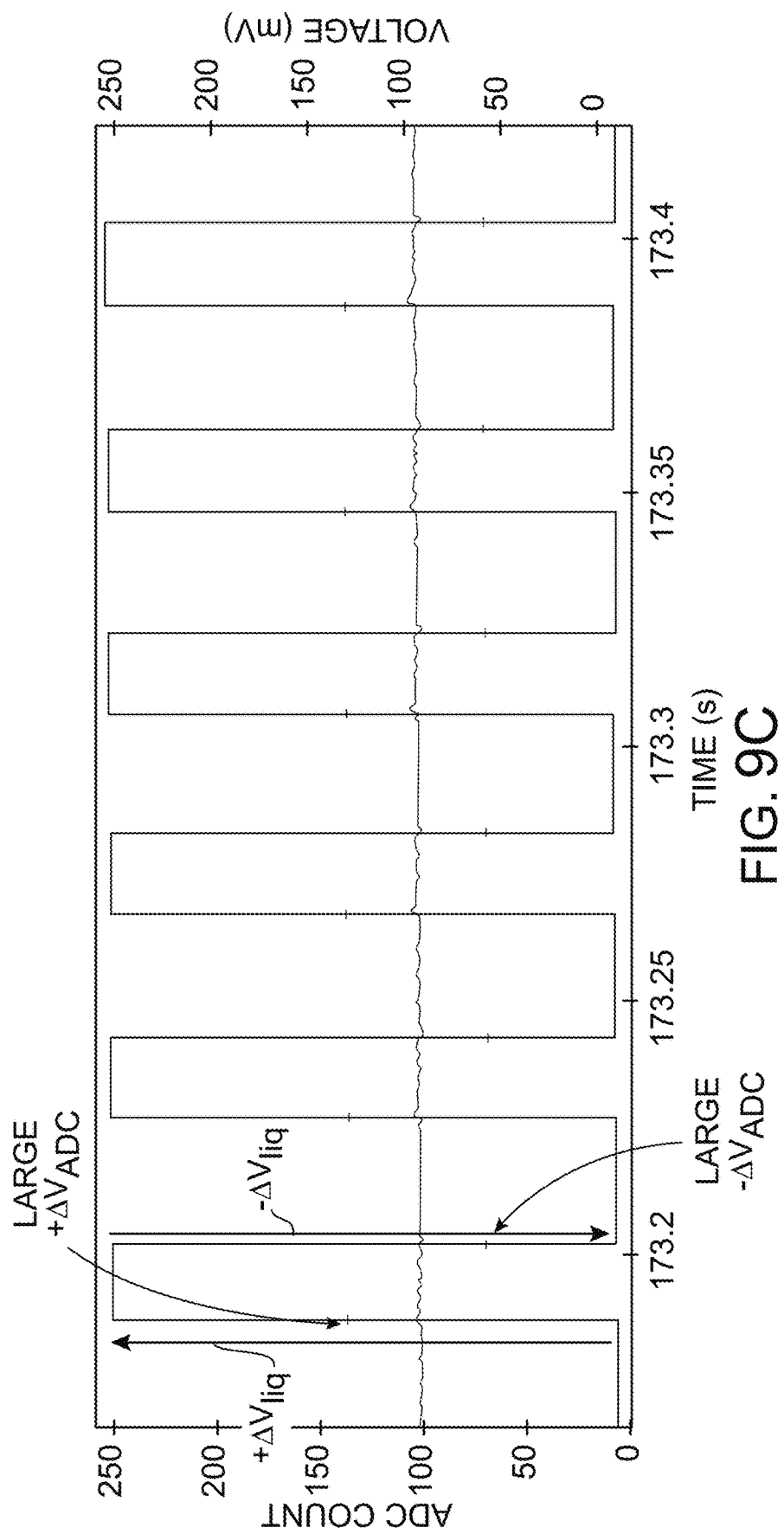
FIG. 9C illustrates a zoomed-in view of the exemplary plot of $V_{ADC}$ versus time (see FIG. 9A) during the time period $t_2$ when a lipid bilayer has been formed.

FIG. 9C illustrates a zoomed-in view of the exemplary plot of $V_{ADC}$ versus time (see FIG. 9A) during the time period $t_2$ when a lipid bilayer has been formed. The results shown in FIG. 9C are consistent with FIG. 8B. In FIG. 9C, at the instance when $\Delta V_{liq}$ is at a positive maximum, a large $+\Delta V_{ADC}$ can be observed between two consecutive sample points because a lipid bilayer has already been formed in the cell. At the instance when $\Delta V_{liq}$ is at a negative maximum, a large $-\Delta V_{ADC}$ can be observed because a lipid bilayer has already been formed in the cell. Note that shortly after the square wave $V_{liq}$ changes from one phase to another, $\Delta V_{liq}$ stays at zero, and $V_{ADC}$ reduces to zero in response. As shown in FIG. 9C, when a lipid bilayer has already been formed in the cell, a positive or negative spike in $V_{ADC}$ can be observed. The positive or negative spikes are followed by much smaller $V_{ADC}$ values.

When a lipid solvent mixture is first deposited into the cells to form the lipid bilayers, lipid bilayers are spontaneously formed in some of the cells, but in other cells there is merely a thick lipid membrane with multiple layers of lipid molecules combined with the solvent spanning across each of the wells of the cells. In order to increase the yield of the nanopore based sequencing chip (i.e., the percentage of cells in the nanopore based sequencing chip with properly formed lipid bilayers and nanopores), the nanopore based sequencing chip may perform additional steps to facilitate the formation of lipid bilayers in additional cells. Therefore, improved techniques for forming lipid bilayers in the cells of a nanopore based sequencing chip would be desirable.

In the present application, improved techniques of forming lipid bilayers in the cells of a nanopore based sequencing chip for analyzing molecules are disclosed. One of the improved techniques applies one or more lipid bilayer initiating stimuli. Different types of lipid bilayer initiating stimuli may be applied, as will be described in greater detail below. For example, mechanical, electrical, or physical stimuli may be applied. Those of ordinary skill in the art will appreciate that other types of stimuli may be suitable for use with the present invention. One or more types of lipid bilayer initiating stimuli may be applied simultaneously, or in different order. The one or more types of lipid bilayer initiating stimuli may be applied in a process that repeats a plurality of time.

A lipid bilayer initiating stimulus facilitates the creation of a small lipid bilayer on a thick lipid membrane. Once a small transient lipid bilayer on a thick lipid membrane is formed, the application of additional lipid bilayer initiating stimuli acts as a positive feedback to continue to enlarge the surface area of the lipid bilayer. As a result, the time required to form lipid bilayers in the cells of the nanopore based sequencing chip can be significantly reduced.

One type of lipid bilayer initiating stimulus is a mechanical stimulus, such as a vibration stimulus. Mechanical vibrations of a thick lipid membrane will cause the lipid molecules to rearrange and move around each other, thereby promoting the self-assembly of some lipid molecules into a two-layered sheet, with the tails pointing towards the center of the sheet to form a small area of lipid bilayer. In some embodiments, vibration of the lipid membrane may be introduced by generating waves in the bulk electrolyte (see bulk electrolyte 114 in FIG. 1 and bulk electrolyte 508 in FIG. 5) contained in the external reservoir (see external reservoir 522 in FIG. 5). For example, a wave generator, acoustic pump, or fluidic pump may be coupled to the flow chamber to generate waves in the bulk electrolyte contained in the external reservoir.

Another type of lipid bilayer initiating stimulus is an electrical stimulus. Applying an electrical lipid bilayer initiating stimulus to the cells that have not had lipid bilayers formed therein yet can improve the efficiency of liquid flow above the thick lipid membranes, thereby facilitating the removal of any excess lipid solvent such that the thick lipid membranes can be thinned out and transitioned into lipid bilayers more efficiently. Applying the electrical lipid bilayer initiating stimulus to the cells that have not had lipid bilayers formed therein yet will also create electrostatic forces that tend to squeeze out the excess lipid solvent and thin out the thick lipid membranes into lipid bilayers. On the other hand, the cells that have already had lipid bilayers properly formed therein should not be further exposed to the same electrical lipid bilayer initiating stimulus, as the electrical stimulus may cause some of the thin lipid bilayers to break down. Therefore, it is advantageous to use the non-destructive technique described in the present application to detect and separate the portion of the cells in the nanopore based sequencing chip that have lipid bilayers formed therein from the portion of the cells that do not have lipid bilayer properly formed therein yet. By dividing the cells into different groups, the cells in different groups can be processed differently, thereby achieving greater efficiency and increasing the overall yield of the nanopore based sequencing chip.

Another type of lipid bilayer initiating stimulus is a physical stimulus. For example, flowing a salt/electrolyte buffer solution through the cells of the nanopore based sequencing chip via a flow chamber facilitates the formation of a lipid bilayer over each of the cells. The salt buffer solution flowed over the cells facilitates the removal of any excess lipid solvent such that the thick lipid membranes can be thinned out and transitioned into lipid bilayers more efficiently. In some embodiments, a salt buffer solution is flowed for a period of two seconds. However, other predetermined period of time may be used as well. The buffer solution flowing cycle may be repeated a number of times. However, it has been found that the number of buffer solution flowing cycles needed to obtain a satisfactory yield of the nanopore based sequencing chip may be as high as tens or hundreds of cycles.

One of the improved techniques applies a salt/electrolyte buffer solution flow over the lipid membrane with a lower osmolarity/osmotic concentration than the osmolarity of the salt buffer solution below the lipid membrane in order to introduce an osmotic imbalance between the salt buffer solution above and below the lipid membrane, which causes the lipid solvent membrane to bow upwards. With the lipid membrane pushed outward from the well, a greater contact surface area of the lipid membrane is exposed to the flow of the salt buffer solution and, as a result, the flow of the salt buffer solution can more effectively remove any excess lipid solvent, such that the thick lipid membrane can be thinned out and transitioned into a lipid bilayer more efficiently. This technique has many advantages, including reducing the time to form lipid bilayers and increasing the efficiency and yield of the nanopore based sequencing chip.

Figure 10B:
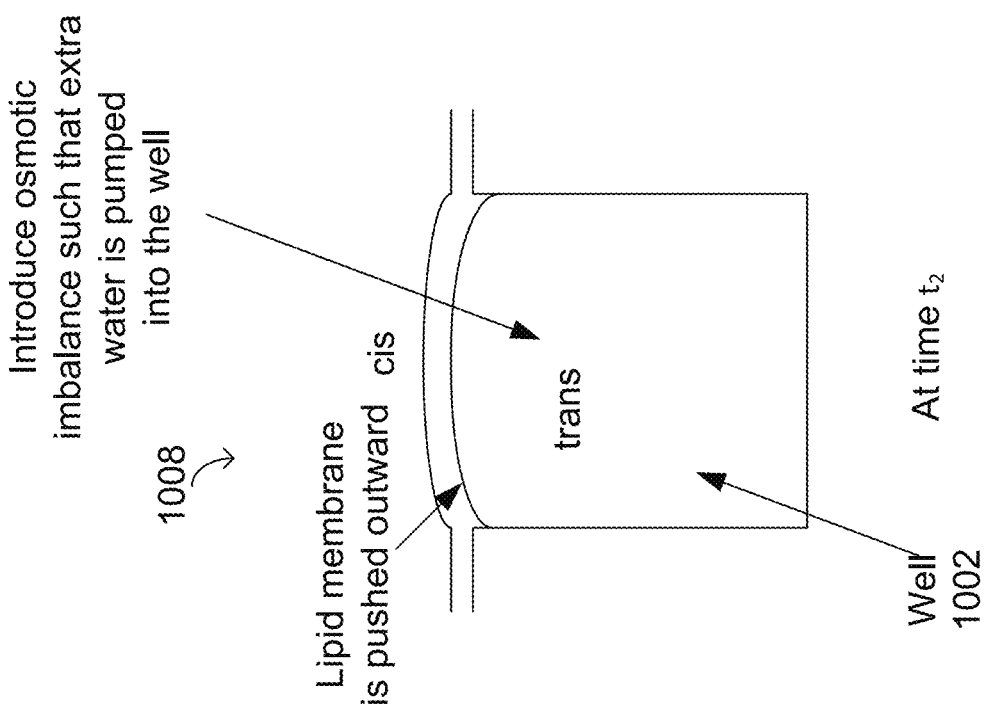
FIG. 10 (including FIGS. 10A and 10B) illustrates an embodiment in which an osmotic imbalance is introduced between the salt buffer solution above and below the lipid membrane, which causes the lipid solvent membrane to bow upwards.
Figure 10A:
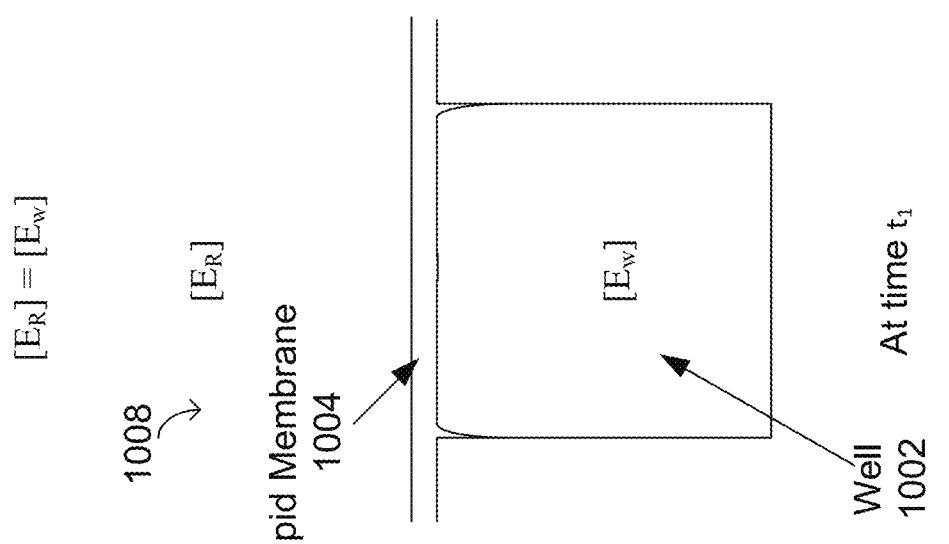

FIG. 10 (including FIGS. 10A and 10B) illustrates an embodiment in which an osmotic imbalance is introduced between the salt buffer solution above and below the lipid membrane, which causes the lipid solvent membrane to bow upwards.

FIG. 10A illustrates that initially at time $t_1$, when a lipid solvent mixture is first deposited into a cell to form a lipid bilayer, the cell merely has a thick lipid membrane 1004 with multiple layers of lipid molecules combined with the solvent spanning across the well 1002 of the cell. The lipid membrane 1004 seals the well from a reservoir 1008 external to the well. Initially at time $t_1$, the osmolarity of the salt/electrolyte solution within the well, $[E_W]$, is the same as the osmolarity of the bulk electrolyte solution in the external reservoir, $[E_R]$. Osmolarity, also known as osmotic concentration, is a measure of solute concentration. Osmolarity measures the number of osmoles of solute particles per unit volume of solution. An osmole is a measure of the number of moles of solute that contribute to the osmotic pressure of a solution. Osmolarity allows the measurement of the osmotic pressure of a solution and the determination of how the solvent will diffuse across a semipermeable membrane (osmosis) separating two solutions of different osmotic concentration.

FIG. 10B illustrates that at later time $t_2$, by flowing over a lipid membrane a lower concentration of electrolyte solution than is initially present in the well while the lipid membrane is in place between the well and the external reservoir, excess water is forced into the well, causing the lipid membrane to bow upwards.

Figure 11:
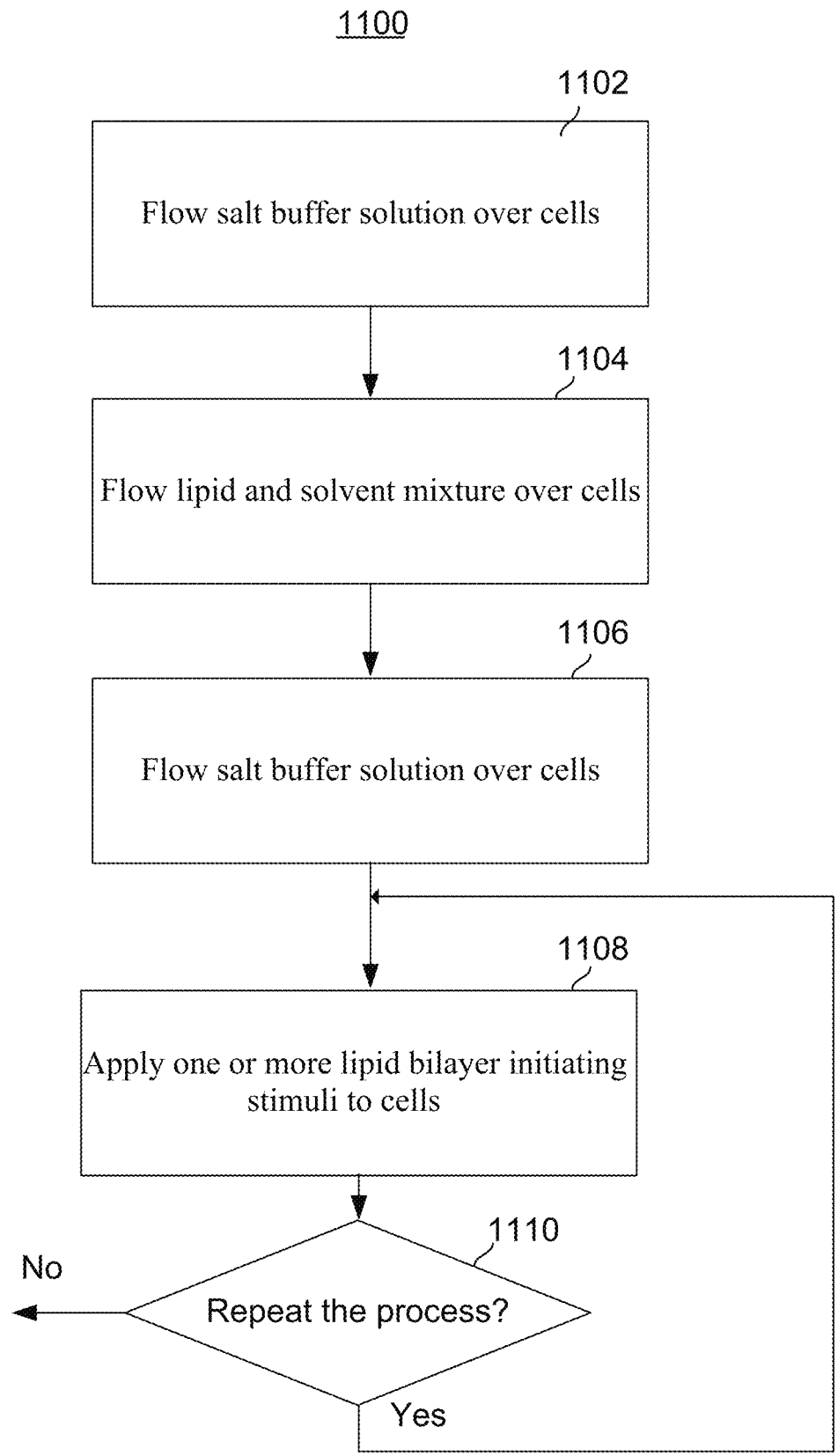
FIG. 11 illustrates an embodiment of a process 1100 for an improved technique of forming lipid bilayers in the cells of a nanopore based sequencing chip.

FIG. 11 illustrates an embodiment of a process 1100 for an improved technique of forming lipid bilayers in the cells of a nanopore based sequencing chip. Process 1100 applies one or more different types of lipid bilayer initiating stimuli. One or more types of lipid bilayer initiating stimuli may be applied simultaneously, or in different order. The one or more types of lipid bilayer initiating stimuli may be applied in process 1100 that repeats a plurality of time. In some embodiments, the nanopore based sequencing chip of FIG. 11 includes a plurality of cells 100 of FIG. 1. In some embodiments, the nanopore based sequencing chip of FIG. 11 includes a plurality of cells 500 of FIG. 5. In some embodiments, the nanopore based sequencing chip of FIG. 11 includes circuitries 600 of FIGS. 6A and 6B.

Process 1100 includes steps in which different types of fluids (e.g., liquids or gases) are flowed through the cells of the nanopore based sequencing chip via a flow chamber. Multiple fluids with significantly different properties (e.g., compressibility, hydrophobicity, and viscosity) are flowed over an array of sensors on the surface of the nanopore based sequencing chip. For improved efficiency, each of the sensors in the array should be exposed to the fluids in a consistent manner. For example, each of the different types of fluids should be flowed over the nanopore based sequencing chip such that the fluid may be delivered to the chip, evenly coating and contacting each of the cells' surfaces, and then delivered out of the chip. As described above, a nanopore based sequencing chip incorporates a large number of sensor cells configured as an array. As the nanopore based sequencing chip is scaled to include more and more cells, achieving an even flow of the different types of fluids across the cells of the chip becomes more challenging.

Figure 12:
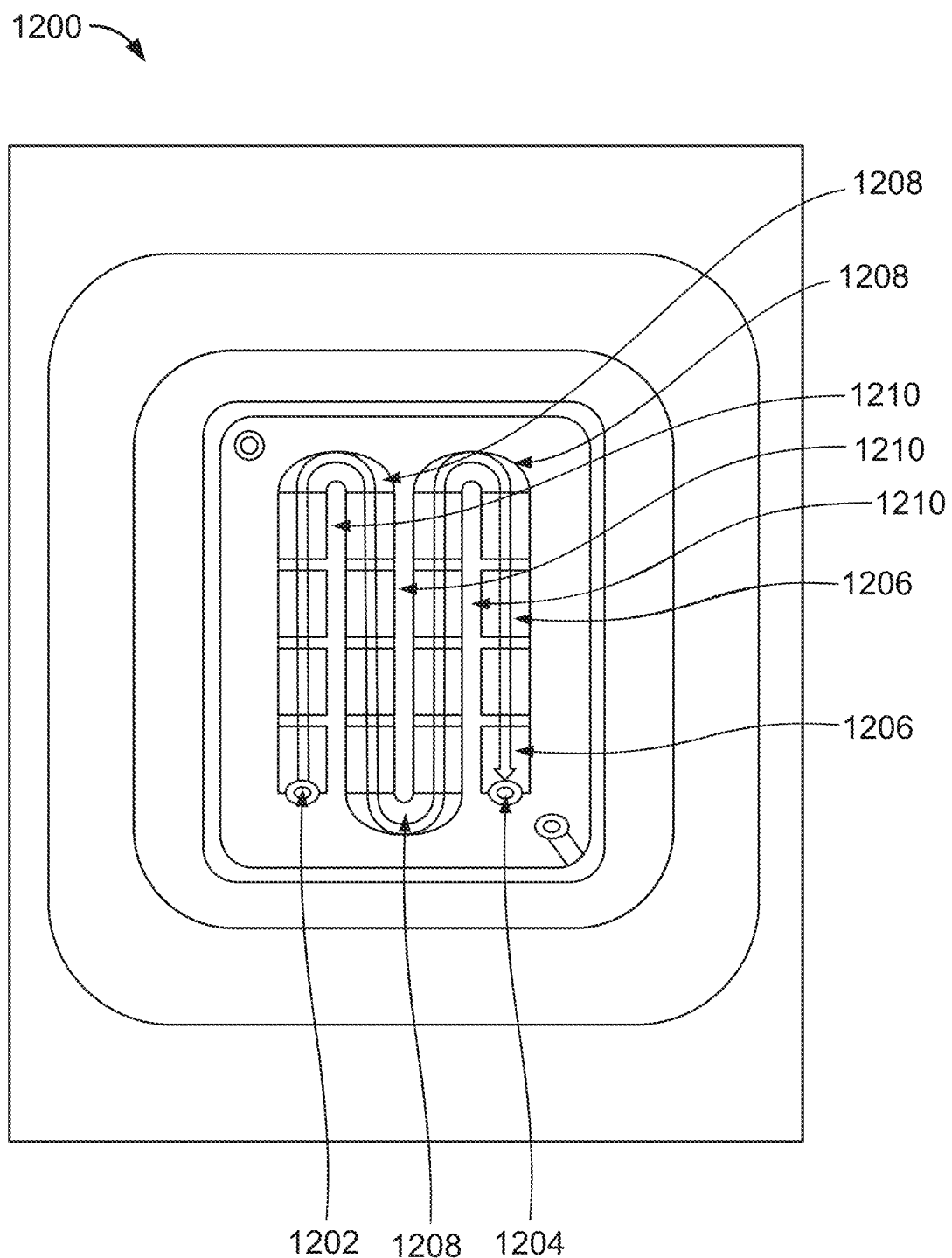
FIG. 12 illustrates the top view of a nanopore based sequencing system 1200 with an improved flow chamber enclosing a silicon chip that allows liquids and gases to pass over and contact sensors on the chip surface.

In some embodiments, the nanopore based sequencing system that performs process 1100 of FIG. 11 includes an improved flow chamber having a serpentine fluid flow channel that directs the fluids to traverse over different sensors of the chip along the length of the channel. FIG. 12 illustrates the top view of a nanopore based sequencing system 1200 with an improved flow chamber enclosing a silicon chip that allows liquids and gases to pass over and contact sensors on the chip surface. The flow chamber includes a serpentine or winding flow channel 1208 that directs the fluids to flow directly above a single column (or a single row) of sensor banks 1206 (each bank including several thousands of sensor cells) from one end of the chip to the opposite end and then directs the fluids to repeatedly loop back and flow directly above other adjacent columns of sensor banks, until all of the sensor banks have been traversed at least once. As shown in FIG. 12, system 1200 includes an inlet 1202 and an outlet 1204.

With reference to FIG. 12, a fluid is directed into system 1200 through inlet 1202. Inlet 1202 may be a tube or a needle. For example, the tube or needle may have a diameter of one millimeter. Instead of feeding the liquid or gas directly into a wide flow chamber with a single continuous space, inlet 1202 feeds the liquid or gas into a serpentine flow channel 1208 that directs the liquid or gas to flow directly above a single column of sensor banks 1206. The serpentine channel 1208 may be formed by stacking together a top plate and a gasket with dividers 1210 that divide the chamber into the serpentine channel to form a flow cell, and then mounting the flow cell on top of the chip. Once the liquid or gas flows through the serpentine channel 1208, the liquid or gas is directed up through outlet 1204 and out of system 1200.

System 1200 allows the fluids to flow more evenly on top of all the sensors on the chip surface. The channel width is configured to be narrow enough such that capillary action has an effect. More particularly, the surface tension (which is caused by cohesion within the fluid) and adhesive forces between the fluid and the enclosing surfaces act to hold the fluid together, thereby preventing the fluid or the air bubbles from breaking up and creating dead zones. For example, the channel may have a width of 1 millimeter or less. The narrow channel enables controlled flow of the fluids and minimizes the amount of remnants from a previous flow of fluids or gases.

With reference to FIG. 11, at 1102, a salt/electrolyte buffer solution is flowed through the cells of the nanopore based sequencing chip via the flow chamber to substantially fill the wells in the cells with the salt buffer solution. As further described herein, the salt buffer solution may include at least one of the following osmolytes: lithium chloride (LiCl), sodelectium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$). The salt buffer solution may also include osmolytes (compounds affecting osmosis) that are not simple ionic salts, including trimethylamine N-oxide (TMAO), proline, trehalose, and the like. In some embodiments, the concentration of the salt buffer solution is 2 M (molar).

At 1104, a lipid and solvent mixture is flowed through the cells of the nanopore based sequencing chip via the flow chamber. In some embodiments, the lipid and solvent mixture includes lipid molecules such as diphytanoylphosphatidylcholine or 1,2-diphytanoyl-sn-glycero-3-phosphocholine (DPhPC), and 1,2-di-O-phytanyl-sn-glycero-3-phosphocholine (DOPhPC). In some embodiments, the lipid and solvent mixture includes decane or tridecane. When the lipid and solvent mixture is first deposited into the cells to form the lipid bilayers, some of the cells have lipid bilayers spontaneously formed, but some of the cells merely have a thick lipid membrane (with multiple layers of lipid molecules and solvent combined together) spanning across each of the wells of the cells.

At 1106, a salt/electrolyte buffer solution is flowed through the cells of the nanopore based sequencing chip via the flow chamber to substantially fill the external reservoir with the salt buffer solution.

At 1108, in order to increase the yield of the nanopore based sequencing chip (i.e., the percentage of cells in the nanopore based sequencing chip with properly formed lipid bilayers and nanopores), the nanopore based sequencing chip may apply one or more types of lipid bilayer initiating stimuli to facilitate the formation of lipid bilayers in additional cells. As described above, one or more types of lipid bilayer initiating stimuli may be applied simultaneously, or in different orders, during a lipid bilayer initiating stimulus phase (step 1108), which may be repeated (determined by step 1110) a plurality of times.

Figure 13:
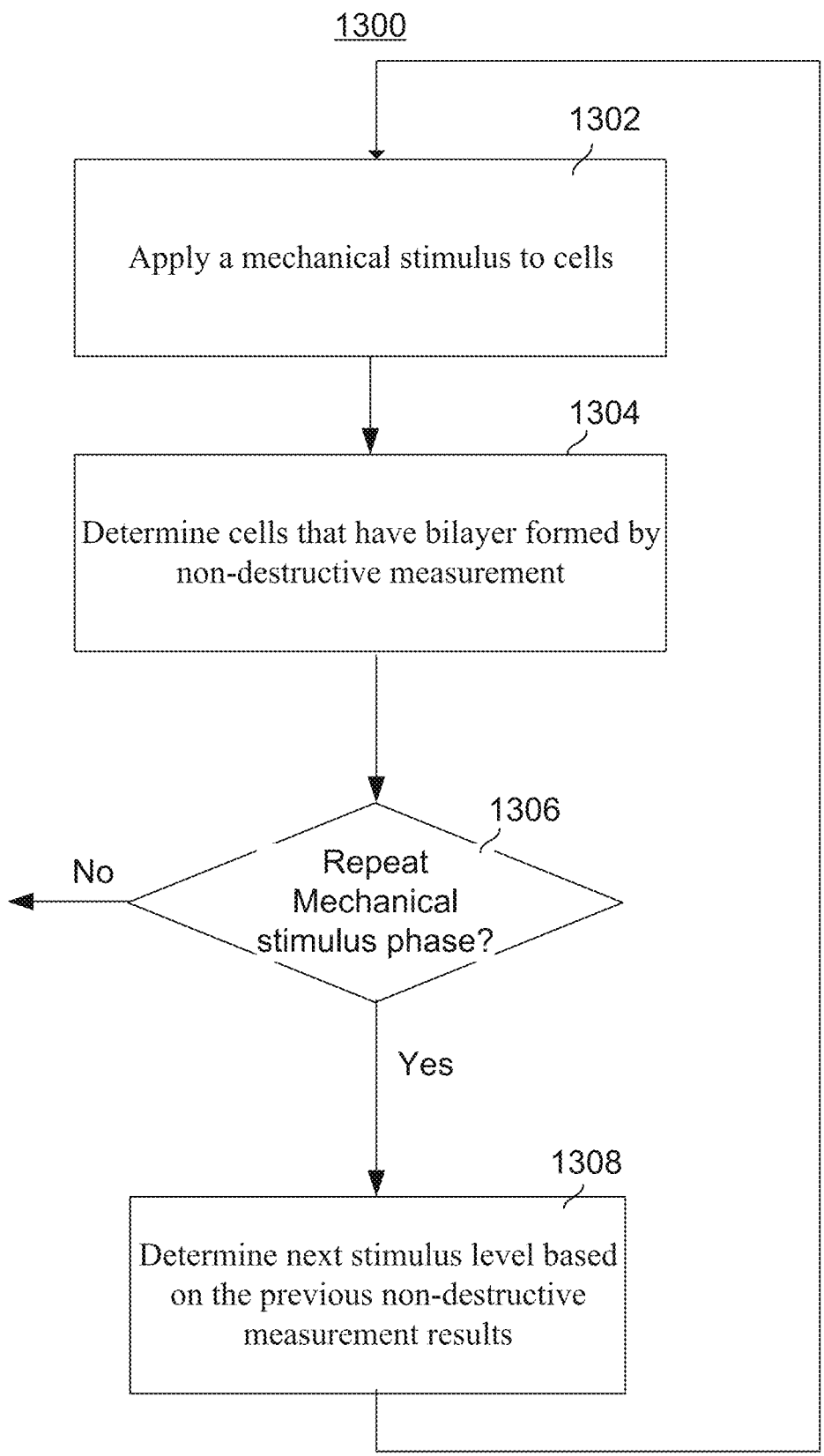
FIG. 13 illustrates an embodiment of a process 1300 for applying a mechanical lipid bilayer initiating stimulus, such as a vibration stimulus, during the lipid bilayer initiating stimulus phase at step 1108 of process 1100.

FIG. 13 illustrates an embodiment of a process 1300 for applying a mechanical lipid bilayer initiating stimulus, such as a vibration stimulus, during the lipid bilayer initiating stimulus phase at step 1108 of process 1100. At 1302, a mechanical lipid bilayer initiating stimulus is applied. Mechanical vibrations of a thick lipid membrane will cause the lipid molecules to rearrange and move around each other, thereby promoting the self-assembly of some lipid molecules into a two-layered sheet, with the tails pointing towards the center of the sheet to form a small area of lipid bilayer. In some embodiments, vibration of the lipid membrane may be introduced by generating waves in the bulk electrolyte (see bulk electrolyte 114 in FIG. 1 and bulk electrolyte 508 in FIG. 5) contained in the external reservoir (see external reservoir 522 in FIG. 5). For example, a wave generator, acoustic pump, or fluidic pump may be coupled to the flow chamber to generate waves in the bulk electrolyte contained in the external reservoir.

At 1304, the non-destructive technique described in the present application is used to detect whether a lipid bilayer is formed in a cell using circuitry 600 of FIG. 6A and FIG. 6B. The detection includes monitoring a voltage change, $\Delta V_{ADC}$, at integrating capacitor 608 ($n_{cap}$) in response to a voltage change ($\Delta V_{liq}$) applied to the bulk liquid in contact with the lipid membrane/bilayer. Cells that have lipid bilayers detected are separated into a different group from the cells that do not have lipid bilayers detected.

At 1306, it is determined whether the mechanical stimulus phase should be repeated. Different criteria may be used at this step. In some embodiments, the mechanical stimulus phase is performed a predetermined number of times. In some embodiments, the mechanical stimulus phase is repeated until a target yield for the nanopore based sequencing chip has been reached. In some embodiments, if the incremental number or percentage of cells that have just been detected as having lipid bilayers formed during the last round of thinning by the stimulus is lower than a predetermined threshold, then process 1300 is terminated.

Process 1300 proceeds to step 1308 if the mechanical stimulus phase is going to be repeated next. At step 1308, the next mechanical stimulus level to be applied is determined. In some embodiments, the mechanical stimulus level is increased by a fixed predetermined amount. In some embodiments, if the incremental number or percentage of cells that have just been detected as having lipid bilayers formed during the last iteration is lower than a predetermined threshold, then the mechanical stimulus level is increased by a fixed predetermined amount; otherwise, the previous mechanical stimulus is found to be effective and thus the same mechanical stimulus level is used again. Process 1300 then proceeds to 1302 and the process is repeated.

Figure 14:
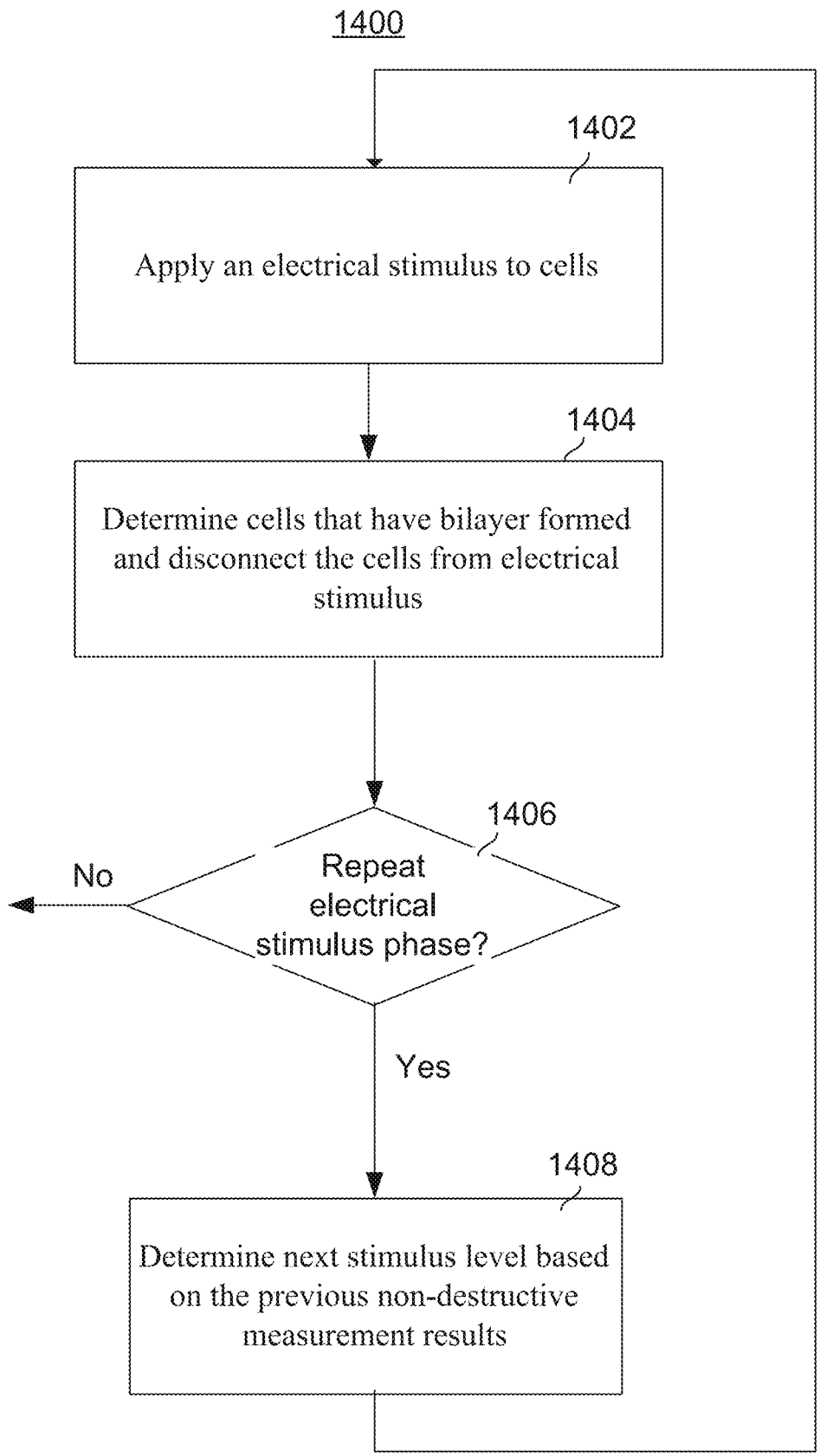
FIG. 14 illustrates an embodiment of a process 1400 for applying an electrical lipid bilayer initiating stimulus during the lipid bilayer initiating stimulus phase at step 1108 of process 1100.

FIG. 14 illustrates an embodiment of a process 1400 for applying an electrical lipid bilayer initiating stimulus during the lipid bilayer initiating stimulus phase at step 1108 of process 1100. At 1402, an electrical lipid bilayer initiating stimulus is applied. Applying the electrical stimulus to the cells that have not had lipid bilayers formed therein yet can improve the efficiency of liquid flow above the thick lipid membranes, thereby facilitating the removal of any excess lipid solvent such that the thick lipid membranes can be thinned out and transitioned into lipid bilayers more efficiently. Applying the electrical stimulus to the cells that have not had lipid bilayers formed therein yet will also create electrostatic forces that tend to squeeze out the excess lipid solvent and thin out the thick lipid membranes into lipid bilayers. In some embodiments, the same circuitry 600 of FIG. 6A and FIG. 6B may be used to apply the electrical stimulus. The only difference in the setup of circuitry 600 between lipid bilayer detection and lipid thinning/lipid bilayer initiating is that the absolute magnitude of $V_{liq}$ is lower for lipid bilayer detection. For example, the absolute magnitude $V_{liq}$ for lipid bilayer detection may be between 100 mV to 250 mV, while the absolute magnitude $V_{liq}$ for lipid thinning may be between 250 mV to 500 mV.

At 1404, the non-destructive technique described in the present application is used to detect whether a lipid bilayer is formed in a cell using circuitry 600 of FIG. 6A and FIG. 6B. The detection includes monitoring a voltage change, $\Delta V_{ADC}$, at integrating capacitor 608 ($n_{cap}$) in response to a voltage change ($\Delta V_{liq}$) applied to the bulk liquid in contact with the lipid membrane/bilayer. Cells that have lipid bilayers detected are separated into a different group from the cells that do not have lipid bilayers detected. Within each of the cells with lipid bilayers detected, pass device 606 is opened in order to disconnect the lipid bilayer and the electrodes from the measurement circuitry 600, such that any electrical lipid bilayer initiating stimulus (if applied to the chip) is disabled from being applied to the cell.

At 1406, it is determined whether the electrical stimulus phase should be repeated. Different criteria may be used at this step. In some embodiments, the electrical stimulus phase is performed a predetermined number of times. In some embodiments, the electrical stimulus phase is repeated until a target yield for the nanopore based sequencing chip has been reached. In some embodiments, if the incremental number or percentage of cells that have just been detected as having lipid bilayers formed during the last round of thinning by the stimulus is lower than a predetermined threshold, then process 1400 is terminated.

Process 1400 proceeds to step 1408 if the electrical stimulus phase is going to be repeated next. At step 1408, the next electrical stimulus level to be applied is determined. In some embodiments, the electrical stimulus level is increased by a fixed predetermined amount. In some embodiments, if the incremental number or percentage of cells that have just been detected as having lipid bilayers formed during the last iteration is lower than a predetermined threshold, then the electrical stimulus level is increased by a fixed predetermined amount; otherwise, the previous electrical stimulus is found to be effective and thus the same electrical stimulus level is used again. Process 1400 then proceeds to 1402 and the process is repeated.

Figure 15:
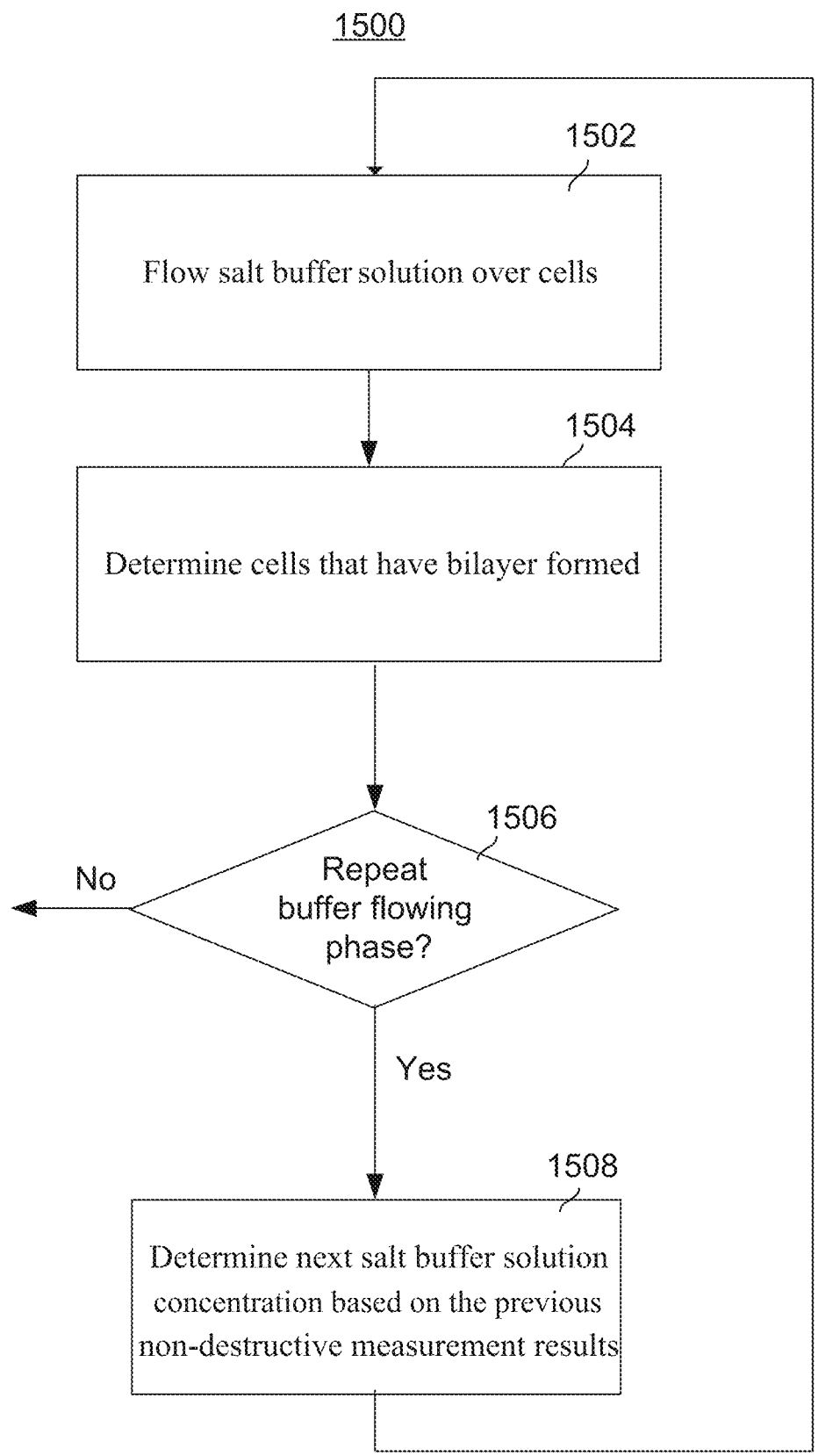
FIG. 15 illustrates an embodiment of a process 1500 for applying a physical lipid bilayer initiating stimulus during the lipid bilayer initiating stimulus phase at step 1108 of process 1100.

FIG. 15 illustrates an embodiment of a process 1500 for applying a physical lipid bilayer initiating stimulus during the lipid bilayer initiating stimulus phase at step 1108 of process 1100. At 1502, a salt/electrolyte buffer solution is flowed through the cells of the nanopore based sequencing chip via the flow chamber. The concentration or osmolarity of the salt electrolyte buffer solution is determined by process 1500 so as to introduce an osmotic imbalance between the electrolyte solution above and below the lipid membrane. By flowing over a lipid membrane a lower concentration of electrolyte solution than is initially present in the well while the lipid membrane is in place between the well and the external reservoir, excess water is forced into the well, causing the lipid membrane to bow upwards. With the lipid membrane pushed outward from the well, a greater contact surface area of the lipid membrane is exposed to the flow of the salt buffer solution and, as a result, the flow of the salt buffer solution can more effectively remove any excess lipid solvent such that the thick lipid membrane can be thinned out and transitioned into a lipid bilayer more efficiently.

For example, the salt electrolyte buffer solution that is flowed through the cells of the nanopore based sequencing chip via the flow chamber at step 1502 has a lower concentration (e.g., 500 mM) than the electrolyte solution that is present in the well (e.g., 2 M), creating a osmolarity difference of 1.5 M. In response to the lower concentration electrolyte solution flowing in the external reservoir (i.e., on the cis side of the lipid membrane), water diffuses across the lipid membrane from the reservoir into the well in order to equalize the concentration on the cis and trans sides of the lipid membrane. This equalization takes place almost instantaneously, since the water molecules readily flow through the lipid membrane. The concentrations on both sides of the lipid membrane equalize to that of the cis side (e.g., 500 mM) since the volume of the external reservoir is significantly greater than that of the trans side (the well). This effectively increases the volume of water under the lipid membrane in the well, causing the lipid membrane to bow upwards, as shown in FIG. 10B.

As shown above, since water may diffuse across the lipid membranes and the salt electrolyte buffer solution that is flowed through the cells may introduce different osmolytes into the external reservoir over time, both the volume and the osmolyte content of the liquid held in the external reservoir and the wells may change over time. It is recognized that the external reservoir may be characterized by a first reservoir osmolarity, which is the osmolarity of the liquid contained in the external reservoir at a specific time. A well in a cell may also be characterized by a second reservoir osmolarity, which is the osmolarity of the liquid contained in the well and confined by the lipid bilayer at a specific time.

At 1504, the non-destructive technique described in the present application is used to detect whether a lipid bilayer is formed in a cell using circuitry 600 of FIG. 6A and FIG. 6B. The detection includes monitoring a voltage change, $\Delta V_{ADC}$, at integrating capacitor 608 ($n_{cap}$) in response to a voltage change ($\Delta V_{liq}$) applied to the bulk liquid in contact with the lipid membrane/bilayer. Cells that have lipid bilayers detected are separated into a different group from the cells that do not have lipid bilayers detected.

At 1506, it is determined whether the salt buffer solution flowing phase should be repeated. Different criteria may be used at this step. In some embodiments, the salt buffer solution flowing phase is performed a predetermined number of times. In some embodiments, the phase is repeated until a target yield for the nanopore based sequencing chip has been reached. In some embodiments, if the incremental number or percentage of cells that have just been detected as having lipid bilayers formed during the last round of thinning by the buffer solution flow is lower than a predetermined threshold, then process 1500 is terminated.

Process 1500 proceeds to step 1508 if the salt buffer solution flowing phase of process 1500 is going to be repeated next. At step 1508, the next salt buffer solution concentration to be applied is determined. For example, the concentration of the salt buffer solution may be progressively increased from the concentration used in the last iteration of step 1502. The concentration of the salt buffer solution is progressively increased because as the salt buffer solution flowing phase is repeated a number of times, more and more lipid bilayers are formed and a smaller difference of concentration between the electrolyte solution above and below the lipid membrane will ensure that the lipid bilayers are not burst by the excess water forced into the wells. Process 1500 then proceeds to 1502 and the process is repeated.

Figure 16B:
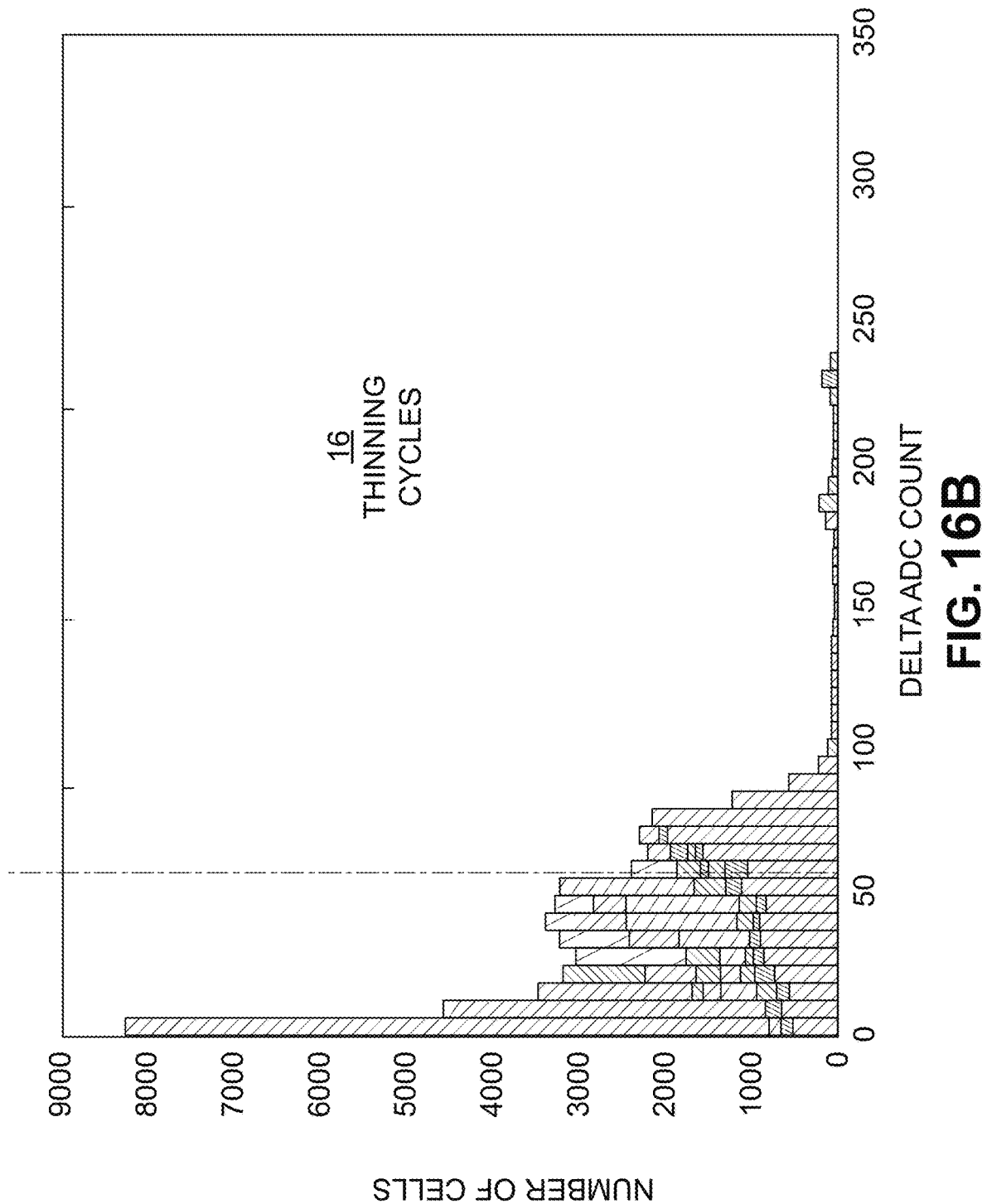
FIG. 16B is a histogram that illustrates that with the introduction of an osmotic imbalance between the salt buffer solution above and below the lipid membrane, 16 salt buffer solution flow cycles achieves a greater overall percentage of cells in the nanopore based sequencing chip with properly formed lipid bilayers.

FIG. 16A is a histogram illustrating that without the introduction of an osmotic imbalance between the salt buffer solution above and below the lipid membrane, salt buffer solution needs to be flowed many times (93 times) before the overall percentage of cells in the nanopore based sequencing chip with properly formed lipid bilayers (i.e., the yield of the nanopore based sequencing chip) is increased to an acceptable threshold. FIG. 16B is a histogram illustrating that with the introduction of an osmotic imbalance between the salt buffer solution above and below the lipid membrane, 16 salt buffer solution flow cycles achieves a greater overall percentage of cells in the nanopore based sequencing chip with properly formed lipid bilayers.

For each of the figures, the x-axis is the voltage change at integrating capacitor 608 ($n_{cap}$), $\Delta V_{ADC}$, in response to a voltage change ($\Delta V_{liq}$) applied to the bulk liquid in contact with the lipid membrane/bilayer, while the y-axis is the number of cells with its $\Delta V_{ADC}$ value within certain $\Delta V_{ADC}$ bins. In this example, cells that have a $\Delta V_{ADC}$ value of 50 or above are determined as having lipid bilayers formed therein. Comparing FIG. 16A and FIG. 16B, with the introduction of an osmotic imbalance between the salt buffer solution above and below the lipid membrane, even with fewer salt buffer solution flow cycles, a high majority of the cells in the nanopore based sequencing chip have lipid bilayers detected.

The invention claimed is:

1. A method of forming a plurality of lipid bilayers over an array of cells in a nanopore based sequencing chip, each of the cells comprising a well, the method comprising:
    flowing a first salt buffer solution with a first osmolarity through a flow channel and over a cell in the nanopore based sequencing chip to substantially fill a well in the cell with the first salt buffer solution;
    flowing a lipid and solvent mixture through the flow channel and over the cell to deposit a lipid membrane over the well that encloses the first salt buffer solution in the well;
    flowing a second salt buffer solution with a second osmolarity through the flow channel above the well, wherein the second osmolarity is a lower osmolarity than the first osmolarity such that an osmotic imbalance is created between a first volume inside the well and a second volume outside the well, wherein the osmotic imbalance causes water to diffuse through the lipid membrane into the well, thereby causing the lipid membrane to bow upwards and extend into the flow channel; and
    flowing the second salt buffer solution over the bowed lipid membrane to reduce the thickness of the lipid membrane to form a lipid bilayer.

2. The method of claim 1, further comprising applying a lipid bilayer initiating stimulus to facilitate creation of a small lipid bilayer on the lipid membrane.

3. The method of claim 2, wherein the step of applying the lipid bilayer initiating stimulus is performed in a number of cycles over time, and wherein the lipid bilayer initiating stimulus level is adaptable in the number of cycles.

4. The method of claim 2, wherein the lipid bilayer initiating stimulus comprises a vibration stimulus.

5. The method of claim 4, wherein applying the vibration stimulus comprises generating waves in the second volume outside the well.

6. The method of claim 2, wherein the lipid bilayer initiating stimulus comprises an electrical stimulus.

7. The method of claim 1, wherein the step of flowing the second salt buffer solution with the second osmolarity above the well is performed in a number of cycles over time, and wherein the second osmolarity is progressively increased in the number of cycles.

8. An apparatus for forming a plurality of lipid bilayers over an array of cells in a nanopore based sequencing chip, the system comprising:
    a nanopore based sequencing chip comprising an array of cells, each of the cells comprising a well;
    a flow channel over the array of cells; and
    a processor and memory for storing instructions that, when executed by the processor, is configured to:
        flow a first salt buffer solution with a first osmolarity through the flow channel and over a cell in the nanopore based sequencing chip to substantially fill a well in the cell with the first salt buffer solution;
        flow a lipid and solvent mixture through the flow channel and over the cell to deposit a lipid membrane over the well that encloses the first salt buffer solution in the well; and
        flow a second salt buffer solution with a second osmolarity through the flow channel and above the well, wherein the second osmolarity is a lower osmolarity than the first osmolarity such that an osmotic imbalance is created between a first volume inside the well and a second volume outside the well, wherein the osmotic imbalance causes water to diffuse through the lipid membrane into the well, thereby causing the lipid membrane to bow upwards and extend into the flow channel; and flowing the second salt buffer solution over the bowed lipid membrane to reduce the thickness of the lipid membrane to form a lipid bilayer.

9. The apparatus of claim 8, wherein the processor or the circuitry is further configured to apply a lipid bilayer initiating stimulus to facilitate creation of a small lipid bilayer on the lipid membrane.

10. The apparatus of claim 9, wherein the step of applying the lipid bilayer initiating stimulus is performed in a number of cycles over time, and wherein the lipid bilayer initiating stimulus level is adaptable in the number of cycles.

11. The apparatus of claim 9, wherein the lipid bilayer initiating stimulus comprises a vibration stimulus.

12. The apparatus of claim 9, wherein the lipid bilayer initiating stimulus comprises an electrical stimulus.

13. The apparatus of claim 8, wherein the step of flowing the second salt buffer solution with the second osmolarity above the well is performed in a number of cycles over time, and wherein the second osmolarity is progressively increased in the number of cycles.

* * * * *